(12) United States Patent
Berthelot et al.

(10) Patent No.: US 9,085,715 B2
(45) Date of Patent: Jul. 21, 2015

(54) PROCESS FOR ASSEMBLING TWO SURFACES OR ONE SURFACE WITH A MOLECULE OF INTEREST

(75) Inventors: Thomas Berthelot, Villebon sur Yvette (FR); Guy Deniau, Auffargis (FR); Vincent Huc, Gif sur Yvette (FR); Xuan Tuan Le, Montreal (CA); Fabien Nekelson, Paris (FR); Sébastien Roussel, Soisy sur Seine (FR); Pascal Viel, Meudon (FR)

(73) Assignee: COMMISSARIAT A L'ENERGIE ATOMIQUE, Paris (FR)

( * ) Notice: Subject to any disclaimer, the term of this patent is extended or adjusted under 35 U.S.C. 154(b) by 1027 days.

(21) Appl. No.: 12/385,269

(22) Filed: Apr. 2, 2009

(65) Prior Publication Data

US 2009/0286308 A1 Nov. 19, 2009

(30) Foreign Application Priority Data

Apr. 3, 2008 (FR) .................................. 08 52209
Oct. 27, 2008 (FR) .................................. 08 57269

(51) Int. Cl.
| | | |
|---|---|---|
| B05D 1/36 | (2006.01) |
| B05D 5/00 | (2006.01) |
| C09J 5/02 | (2006.01) |
| G01N 33/543 | (2006.01) |
| G01N 35/00 | (2006.01) |

(52) U.S. Cl.
CPC ............. *C09J 5/02* (2013.01); *G01N 33/54353* (2013.01); *G01N 2035/00158* (2013.01); *Y10T 156/10* (2015.01)

(58) Field of Classification Search
CPC .......................... C29C 35/0888; B29C 59/043
See application file for complete search history.

(56) References Cited

U.S. PATENT DOCUMENTS

| 2005/0031887 A1 | 2/2005 | Finestone et al. |
| 2005/0170195 A1* | 8/2005 | Bureau et al. .............. 428/615 |
| 2005/0186378 A1* | 8/2005 | Bhatt ........................ 428/36.9 |

(Continued)

FOREIGN PATENT DOCUMENTS

| JP | 2001-178472 A | 7/2001 |
| WO | WO 03 080748 A1 | 10/2003 |
| WO | WO 2008/078052 A2 | 7/2008 |

OTHER PUBLICATIONS

Newton et al., (Atomic Force Microscopy Study of the topographic evolution of polyacrylonitrile thin films submitted to a rapid thermal treatment, Thin Solid Films 303, 1997, 200-206).*

(Continued)

*Primary Examiner* — Michael Cleveland
*Assistant Examiner* — Francisco Tschen
(74) *Attorney, Agent, or Firm* — Nixon Peabody LLP

(57) ABSTRACT

The present invention relates to a process for assembling at least one zone of a first surface with at least one zone of a second surface or with a molecule of interest, comprising a step that consists in placing the said zone of the said first surface in contact with the said zone of the said second surface or with the said molecule of interest, the said zone of the said first surface bearing at least one radical and/or ionic species. The present invention also relates to a solid support whose surface bears at least one zone with at least one radical and/or ionic species, with at least one adhesion primer, or with at least one adhesion primer precursor, and to its various uses.

10 Claims, 12 Drawing Sheets

(56) References Cited

U.S. PATENT DOCUMENTS

| | | |
|---|---|---|
| 2007/0281148 A1 | 12/2007 | Bureau et al. |
| 2008/0087550 A1* | 4/2008 | Deniau ............... 205/170 |
| 2008/0124832 A1 | 5/2008 | Deniau et al. |
| 2008/0236666 A1* | 10/2008 | Bidan et al. ............ 136/261 |

OTHER PUBLICATIONS

Matrab et al., Atom transfer radical polymerization (ATRP) initiated by aryl diazonium salts: a new route for surface modification of multiwalled carbon nanotubes (MWCNT) by tethered polymer chains, Colloids and Surfaces A: Physicochem. Eng. Aspects 287, 2006, 217-221.*

Ohkubo et al., Influence of cross-linking monomer and hydrophobic styrene comonomer on stereoselective esterase activities of polymer catalyst imprinted with a transition-state analogue for hydrolysis of amino acid esters, Polymer, 42, 2001, 2263-2266.*

Hong et al., Encapsulation of multi-walled carbon nanotubes by poly(4-vinylpyridine) and its dispersion stability in various solvent media, Synthetic Metals, 158, 2008, 900-907.*

Viel et al (Covalent grafting onto self-adhesive surfaces based on arydiazonium salt seed layers, J.Mater.Chem, 2008, 18, 5913-5920).*

Simionescu et al., Bioactive Polymers XXX. Immobilization of Invertase on the Diazonium Salt of 4-Aminobenzoylcellulose, Biotechnology and Bioengineering, vol. XXIX, pp. 361-365, 1987.*

Mallard et al., "Opto-Electronic DNA Chip: High Performance Chip Reading with an All-Electric Interface", Biosensors and Bioelectronics 20 (2005), pp. 1813-1820.

Delamar et al., Journal of the American Chemical Society, 1992, vol. 114, pp. 5883-5884.

Harper et al., "Maleimide-activated Aryl Diazonium Salts for Electrode Surface Functionalization with Biological and Redox-Active Molecules", Langmuir 2008, vol. 24, pp. 2206-2211.

Rempp et al., "Polymer Synthesis", $2^{nd}$ Revised ed., 1991, pp. 65-91.

Goncalves et al., "Design, Synthesis, and Evaluation of Original Carriers for Targeting Vascular Endothelial Growth Factor Receptor Interactions", Pharmaceutical Research, vol. 22, No. 8, Aug. 2005, pp. 1411-1421.

Baugh et al., Journal American Chemical Society, vol. 123, 2001, pp. 12488-12494.

International Preliminary Report on Patentability in International Application No. PCT/EP2009/053977, mailed Jan. 20, 2011.

Lyskawa, Joel et al., "Direct Modification of a Gold Electrode With Aminophenyl Groups by Electrochemical Reduction of in Situ Generated Aminophenyl Monodiazonium Cations", Chemistry of Materials, vol. 18 (20), pp. 4755-4763, 2006.

Mevellec, Vincent et al., "Grafting Polymers on Surfaces: A New Powerful and Versatile Diazonium Salt-Based One-Step Process in Aqueous Media", Chemistry of Materials, vol. 19 (25), pp. 6323-6330, 2007.

Xu, L. et al., "Stable Multilayer Films Based on Photoinduced Interaction Between Polyoxometalates and Diazo Resin", Materials Letters, vol. 58, pp. 3441-3446, 2004.

* cited by examiner

Graphite

SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Unprotected linear synthetic peptide

<400> SEQUENCE: 1

```
Gly Pro Gly Gly Val Val Gly Pro
1               5
```

<210> SEQ ID NO 2
<211> LENGTH: 17
<212> TYPE: PRT
<213> ORGANISM: Artificial Sequence
<220> FEATURE:
<223> OTHER INFORMATION: Semi-protected synthetic cyclic peptide
      (CBO-P11)
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: CHAIN
<222> LOCATION: (3)..(3)
<223> OTHER INFORMATION: Glutamine bearing a trityl (Trt) protecting
      group
<220> FEATURE:
<221> NAME/KEY: CHAIN
<222> LOCATION: (6)..(6)
<223> OTHER INFORMATION: Arginine bearing a
      2,2,4,6,7-pentamethyldihydrobenzofuran-5-sulfonyl (Pbf)
      protecting group
<220> FEATURE:
<221> NAME/KEY: CHAIN
<222> LOCATION: (8)..(8)
<223> OTHER INFORMATION: Lysine bearing a t-butoxycarbonyl (Boc)
      protecting group
<220> FEATURE:
<221> NAME/KEY: CHAIN
<222> LOCATION: (10)..(10)
<223> OTHER INFORMATION: Histidine bearing a trityl (Trt) protecting
      group
<220> FEATURE:
<221> NAME/KEY: CHAIN
<222> LOCATION: (11)..(11)
<223> OTHER INFORMATION: Glutamine bearing a trityl (Trt) protecting
      group
<220> FEATURE:
<221> NAME/KEY: CHAIN
<222> LOCATION: (13)..(13)
<223> OTHER INFORMATION: Glutamine bearing a trityl (Trt) protecting
      group
<220> FEATURE:
<221> NAME/KEY: CHAIN
<222> LOCATION: (14)..(14)
<223> OTHER INFORMATION: Histidine bearing a trityl (Trt) protecting
      group
<220> FEATURE:
<221> NAME/KEY: CHAIN
<222> LOCATION: (17)..(17)
<223> OTHER INFORMATION: Glutamic acid bearing a -(CH2)2-COOH protecting
      group

<400> SEQUENCE: 2

```
Phe Pro Gln Ile Met Arg Ile Lys Pro His Gln Gly Gln His Ile Gly
1               5                   10                  15

Glu
```

<210> SEQ ID NO 3
<211> LENGTH: 17
<212> TYPE: PRT
<213> ORGANISM: Artificial Sequence
<220> FEATURE:
<223> OTHER INFORMATION: Unprotected synthetic cyclic peptide
<220> FEATURE:
<221> NAME/KEY: MISC_FEATURE
<222> LOCATION: (1)..(1)
<223> OTHER INFORMATION: D-phenylalanine

<400> SEQUENCE: 3

```
Phe Pro Gln Ile Met Arg Ile Lys Pro His Gln Gly Gln His Ile Gly
1               5                   10                  15
Glu
```

PROCESS FOR ASSEMBLING TWO SURFACES OR ONE SURFACE WITH A MOLECULE OF INTEREST

TECHNICAL FIELD

The present invention relates to the field of pre-adhesive surfaces and to assembling and bonding processes. It enables assembly by direct contact between two materials or between one material and molecules. In the case of two materials, the coating material reacts by direct contact (without "adhesive" in the conventional sense) with the first material.

The invention may especially be used for bonding or immobilizing, on a given surface, carbon or graphene nanotubes isolated by exfoliation. The present invention also allows the immobilization, on a given surface, of metal particles, of polymers, of organic molecules, of macromolecules and particularly of biological molecules. In the latter case, the present invention proposes novel biosensors comprising an adhesive face as obtained via the process of the invention, on which are immobilized one or more identical or different components chosen from peptides, polypeptides, proteins such as enzymes, nucleic acids, antibodies or antibody fragments, polysaccharides, cells and cell fragments.

The invention also relates to the use of various surfaces and especially of suitably selected coating finishes, in order to enable the easy and reproducible assembling of various materials or molecules on a coated surface.

PRIOR ART

Microelectronics concerns the study and manufacture of electronic components at the micrometric scale. These components are manufactured from semiconductive materials and minerals, for instance silicon, via various technologies, including photolithography. This technology allows the low-cost integration of numerous electronic functions onto the same piece of silicon (or any other semiconductor). The circuits thus made are known as "chips" or "integrated circuits". However, with the evolution of manufacturing techniques, the size of the components continues to reduce. At the sub-micrometric scale, artifact, which were previously unimportant, are greatly amplified. The signal transmission delays are essentially due to the spurious interconnection capacities of the active components rather than to the delay in crossing these components. The object of research workers and engineers is thus to use novel design methods to limit these effects by improving the size and cost of the components, the transmission speed and the electrical consumption.

It is thus necessary to find novel manufacturing materials and techniques for reducing the size of the components and thus covering the nanometric range. This range is that of organic molecules. The main illustration of molecular electronics is the carbon nanotube. This material has in recent years been the source of a considerable number of scientific publications. A carbon nanotube is a particular crystalline structure, of hollow and occasionally closed tubular shape, composed of carbon atoms regularly arranged in hexagonal lattices.

Carbon nanotubes allow the production of transistors at a level of miniaturization never achieved hitherto. Unfortunately, during their manufacture, both conductive nanotubes and semiconductive nanotubes are obtained, whereas only the latter have advantageous properties. The need to sort nanotubes obtained in order to recover the semiconductive nanotubes has revealed an alternative to carbon nanotubes. This involves using graphite flakes or graphenes. This novel route is in full expansion. A graphene is generally described as an open nanotube. Graphene turns out to be the only component of high-organized-phase graphite (HOPG), which may be represented as a graphene multi-flakes structure. The difficulty consists in succeeding in obtaining a graphene from a block of HOPG or graphite containing several thousand flakes. The technique most commonly used, which consists in flaking or exfoliating the block of HOPG or the graphite by adhesive cleavage, is shown in FIG. 1.

Graphene is particularly advantageous since it is conductive in one direction and semiconductive in another. All graphenes are thus potentially usable. It then remains merely to insert the electrical connections along the correct axis. This process is already mastered. However, the graphene must be immobilized on a surface in order to be used. At the present time, commercial adhesives are used for this immobilization. These procedures lead to the formation of layers of adhesives of variable and poorly controlled thicknesses. Beyond this, the strong mechanical constraints encountered during the exfoliation process are often reflected by tears or folds in the thin graphene flakes. Total detachment from the surface is also liable to occur. Furthermore, adhesion of the graphenes is achieved via physisorption mechanisms that are themselves poorly controlled.

An adhesive is defined as a product that is capable of holding together materials, especially by adhesion. Adhesion is thus the state in which two surfaces are held together via interfacial forces. Adhesives are obtained by formulating several constituents that each provide one or more technological functions, the base resin leading to the name of the adhesive.

The conditions of use of the adhesive (rheology, wettability of the surfaces, etc.) and the final performance qualities of the assembly are especially associated with the intrinsic characteristics of the adhesive, but also with the formulation adjuvants such as plasticizers, surfactants, fillers, etc.; the design of the assembly (geometry of the joints); the preparation of the surfaces and the implementation parameters. There is no universal adhesive, but rather several dozens of families of adhesives.

To overcome this problem, the use of electro-grafting has been proposed in international patent application WO 03/080748. The process allows the fixing of macro-objects onto an electrically conductive or semiconductive surface by electro-grafting using an electrolytic solution comprising, in dissolved, particulate or emulsified form, at least one macro-object constituted of a macrostructural part functionalized with at least one electro-active group capable of bringing about the electro-grafting of the said macro-object onto the surface. The grafting is performed by electrolysis of the solution using the conductive or semiconductive surface to be coated as the working electrode in order to give, by electro-reduction or electro-oxidation of the said solution, a grafted coating of the macro-object or of its condensation products on the said surface. However, this method remains limited to electrically conductive or semiconductive surfaces and it also requires the presence of specific groups at the surface of the objects to be grafted.

In the field of microelectronics, silanes are usually used for modifying a surface by means of chemical grafting of difunctional molecules, which leads to strong bonds between the surface and a species. However, the chemical reactivity of these compounds is low and requires annealing often exceeding 100° C. to immobilize first the silanes on the surface, with the formation of a siloxane bond that nevertheless remains readily hydrolysable, and, subsequently, the coating.

Diazo-resins have been used for forming multiple layers of enzymes or of polyoxometallates on the surface of various materials by electronic complexation and then photoreaction [Materials Letters, 58, 2004, 3441-3446 and Electrochim. Acta. 49, 2004, 4777-4786]. This process remains limited since it requires the existence of electronic interactions between the species intended to be deposited on the surface and the diazo-resins. In addition, it does not appear to allow grafting with the surface.

In the field of biosensors, a wide variety of analytical systems have been developed. These biosensors may use enzymes, proteins, antibodies, nucleic acids, polysaccharides or live cells, in combination with electrochemical, optical, piezoelectric, magnetic or thermal transducers. Biosensors are measuring instruments aimed at accomplishing the detection of a molecule in a sample that is often complex. The crucial phase of molecular recognition is performed by means of the bioreceptor, which is usually an immobilized biological component, forming the sensitive layer. During the molecular recognition, the presence of the target molecule is directly or indirectly reflected by a signal. The signal may be an emission of photons, the appearance of reaction product(s), or a variation in mass, pH or electrical properties. The second phase, known as the transduction/amplification phase, has the role of collecting and transforming this signal into a measurable electrical current. Then, the data may be acquired and processed in the form of numerical values, which represents the third phase of data acquisition and processing. The success of the functioning of a biosensor is closely linked to the satisfactory synergy between the various components of which it is formed: the support, the immobilization method and the detection/transduction system.

The generic term "biochip" includes a set of analytical devices whose technologies are partly derived from the developments made for biosensors. Biochips comprise several recognition components, generally arranged side by side on a given support, with a more or less high density. Thus, a small amount of biomolecules is immobilized on a surface of small size (from a few millimeters to a few centimeters), enabling measurements to be taken on small volumes of samples (from a few nanoliters to a few microliters). Specifically, the operating principle of biochips is based on that of biosensors, with, in addition to the integrated system approach, notions of miniaturization and parallelization. Generally, the biological components are arranged in the form of spots, aligned parallel to the surface of a support. Various categories of biochip exist, including DNA biochips and protein biochips, complemented by peptide and sugar biochips. Within each category, the desired application may be different. It may be envisaged to quantitatively detect the presence of a target molecule (assay) in a complex sample, or to study the interactions of a biomolecule on a set of molecules immobilized in the form of spots (screening).

The support and the nature of the biomolecules to be fixed impacts the immobilization method to be used. Generally, the choice of the support is itself impacted by the detection method that will be used. "Active" supports and "passive" supports, with regard to detection, may thus be distinguished. "Active" supports are conductive materials, used for electrochemical detections and/or immobilizations (amperometry, impedance, electrochemiluminescence), or are optically active (CCD, [Mallard et al., 2005, *Biosensors & Bioelectronics*, 20, 1813-1820]).

The immobilization methods already described and validated may be classified according to the nature of the interactions involved. Among the existing methods are (i) immobilizations without covalent grafting involving an adsorption, (ii) trapping in a gel or a polymer, involving low-energy bonds (of hydrophobic or electrostatic type, or mechanical retention in a network) (iii) "covalent" immobilizations, in which "coupling" chemical reactions lead to the formation of covalent bonds between biomolecules and support.

Adsorption is the simplest method for immobilizing biological components. It involves low-energy interactions between the support and the biomolecules. The adsorption capacity of numerous supports surface-modified with compounds such as methylsilane, polydimethylsiloxane, polystyrene, polyimide, thiosilane, epoxysilane, polyethylene glycol-silane, aminosilane, agarose and alkanethiols depends on the degree of hydrophobicity of the proteins to be immobilized. Other materials may also be used directly for immobilization by adsorption, such as polyvinylidene chloride, acrylonitrile-butadiene-styrene, polydimethylsiloxane, nylon, charged nylon, nitrocellulose or nanoporous silicon. The use of a support which surface has been modified with polylysine, poly(allylamine) hydrochloride or sodium poly(styrenesulfonate) allows adsorption via electrostatic forces.

These trapping methods comprising encapsulation, retention in a gel or a polymer or co-crosslinking are used in various manners. The polymers used may be polyvinyl derivatives, polyethylene glycols, dextran or aminodextran. They may be photopolymerizable, or alternatively electropolymerizable, such as polypyrrole, polythiophene or polyaniline. Co-crosslinking is generally performed between a protein of interest and a neutral protein, usually BSA (bovine serum albumin), and in the presence of a coupling agent, generally glutaraldehyde. The trapping methods generally make it possible to increase the protein charged per unit area.

Affinity immobilization uses the natural properties of recognition and of interaction of certain molecules. Streptavidin/biotin coupling is predominantly used in this type of non-covalent immobilization, given the very strong affinity between these two species ($Kd=10^{-15}$ M). This method consists either in immobilizing streptavidin (homotetrameric protein) or biotin on the surface of a support. The immobilization then takes place indirectly by means of placing in contact protein or another molecule that has been labelled beforehand either with biotin or with streptavidin. It is also possible to use the strong affinity of this streptavidin/biotin couple in order to immobilize particles of large size (polystyrene beads of diameter: 1 μm). The latter technique makes it possible, by means of streptavidin beads bound to a support activated with biotin, to increase the amount of biological material immobilized per unit area. Other proteins such as proteins A and G may be used for their property of specific interaction with antibodies, for example. Biological agents of this type are generally adsorbed onto the surface of polydimethylsiloxane or by precoupling with glutaraldehyde in various hydrophilic polymers (polyethyleneimine, dextran, polyvinyl alcohol, aminodextran and 3-aminopropyltriethoxysilane).

Chemical methods for modifying surfaces are used for covalently fixing proteins and nucleic acids. In this case, the support should have at the surface reactive chemical groups such as hydroxyl, amine, aldehyde, epoxide, carboxyl, azide, alkyne, hydrazone or thiol groups in order to perform coupling reactions. The methods leading to covalent coupling between the support and the biomolecules depend essentially on the nature of the substrate employed. The various methods are presented as a function of the material used as support.

Glass is commonly modified by using silane chemistry. Methods leading to the formation of self-assembled monolayers (SAM) are preferred. These techniques consist in generating a monolayer of alkylsilane compounds, which functionalize the glass surfaces. These silanes have at their terminal functions enabling the creation of a covalent bond with the biological agent, such function may be for example an amine, a carboxylic acid, an aldehyde, an hydroxyl, a thiol, a maleimide or a succinimide ester function.

Among metals, platinum may be preoxidized, before being chemically modified with aminosilanes.

In order to use gold surfaces, the methods leading to the formation of self-assembled monolayers (SAM) are preferred. These techniques consist in generating a monolayer of thiol compounds, which functionalize the gold surfaces. The functionalized gold surface then has properties depending on the chain length and on the functions that are available at their extremity. Thus, the deposited lipids are chosen as a function of the desired properties: immobilization by adsorption, covalent coupling or electrochemical transduction. For the development of supports intended for SPR measurements, two techniques are predominantly used: the chemistry of thiols alone, and the chemistry of thiols bearing polymers of dextran type. In the case of thiol chemistry, the gold surface is chemically treated so as to be functionalized with a monolayer of amine-alkenethiol, which is then used so as to covalently fix the biomolecules to the support. This technique has enabled the development of biochips for detection by SPR imaging (SPRi) using immobilized oligonucleotides, immobilized proteins of low molecular weight and immobilized carbohydrates. Immobilization involving polymers of dextran type is also widely used for the immobilization of biomolecules on gold supports for SPR. This technique is the one used by the company Biacore®. This technique consists in using aminated or oxidized (carboxylic acid) dextran polymers in order to fix the biomolecules via covalent coupling thereto.

The carbon-based surfaces, more particularly based on glassy carbon, may be electrochemically oxidized, so as to produce at the surface reactive oxygenated functions. The conditions required are an acidic medium, and an oxidizing potential (+1.6 V vs-SCE). The carboxyl functions that appear at the surface can then be involved in coupling reactions of carbonyl/primary amine type, especially with cross-linking agents: ethylenediamine alone or ethylenediamine followed by glutaraldehyde. These processes have been used for immobilizing DNA strands, oligonucleotide probes and enzymes.

The company Affymetrix® uses a photolithographic technique that allows the in situ synthesis of nucleotide probes covalently fixed to the surface of a quartz chip (1×1 cm). To do this, chemical coupling reaction steps are performed in sequence, with deprotection steps. These deprotection steps target zones of the chip by means of a photolithography technique: a mask having the appropriate apertures enables the chosen oligonucleotides to be deprotected for the purpose of coupling. This method makes it possible to create chips bearing up to 1.3 million strands (in total), which may represent up to 10 000 different sequence spots.

Supports of polydimethylsiloxane (PDMS) type may also be used for covalent immobilizations. The chemistry used involves the same processes as those used on glass: silane chemistry applied to PDMS, after oxidation steps, either via the oxygen plasma method, or via the methods using hydrogen peroxide in acidic medium. This type of modified support has been able to be functionalized finally with a layer of biotin. The PDMS after oxidation in acidic medium and silanization has enabled the covalent grafting of molecules such as proteins, peptides or oligonucleotides.

The techniques known as "electro-addressing" of biomolecules are recent immobilization methods. First, biomolecules are modified with an electropolymerizable unit. By applying an electrochemical potential to the spots of a screen-printed graphite electrode microarrays, modified biomolecules are electro-addressed to the spots.

Historically, immobilization via electro-addressing is recent technology that appeared with the research conducted on conductive electropolymers. By definition, these are polymeric structures produced by electro-reduction or electro-oxidation from monomers in solution. The polymerized films have conductive properties that originate from electrons high mobility, due to the conjugation of the C=C bonds, along the polymerized chain. The first biosensor using polypyrrole films was based on the trapping of an enzyme, during the process of electropolymerization of pyrrole in solution. This technique exploits the capacity of pyrrole and/or derivatives thereof to form insoluble films, adsorbed onto the surface of the electrode. In this type of system, the polymer not only acts as immobilization matrix for the enzyme, but also enables rapid electron transfer from the enzyme to the electrode. Currently, the immobilization systems using these electropolymers are essentially associated with amperometric detection. The polymers used are of diverse nature: polyaniline, polypyrrole, polyacetylene, polyphenylene or polythiophene.

Among these systems, two major classes of immobilization involving electropolymers may be distinguished. Firstly, the "mechanical" trapping of biomolecules during the electropolymerization process, which is efficient for high molecular weight molecules such as proteins, and secondly, the copolymerization of monomers of pyrrole type with biomolecules functionalized with pyrrole units. The latter immobilization is more efficient for immobilizing "small" biomolecules such as oligonucleotides or polypeptides, but may also be used for high molecular weight molecules.

Enzymes of oxidase type have been immobilized via this technique in conductive electropolymer films: polyaniline, polyindole, polypyrrole and poly(o-phenyldiamine). Enzymes have also been immobilized by electro-addressing, especially an invertase in a mixed film of polypyrrole/PMMA-co-PMMT (polymethyl methacrylate-copolymethyl-thienyl-methacrylate). Similarly, a tyrosinase has been immobilized by trapping in an electro-generated polythiophene film at the surface of a glassy carbon electrode. This method of trapping biomolecules during electropolymerization has also been described for the production of immunoreceptors. More recently, this type of immobilization has been used for producing spots of several electro-addressed antibodies in polypyrrole on a surface of interdigitated microelectrodes.

This second immobilization method also involving these electropolymers is based on the co-electropolymerization of monomers and biomolecules functionalized with a derivative of this monomer. This process is more commonly used for small molecules, and leads to covalent fixing of the biomolecules in the polymer, which avoids releasing problems (desorption . . . ). Thus, amino acids and dipeptides functionalized with pyrrole have been co-electropolymerized in pyrrole films. Using this same co-electropolymerization approach, a biotin derivative has been electro-addressed in a polydicarbazole film at the surface of a glassy carbon electrode. This support then allows the immobilization of an avidin-polyphenol oxidase complex, and thus the detection by amperometry of L- and D-noradrenalin. Moreover, a network of 48 gold electrodes of 50 µm×50 µm each has been used as the basis for the electro-addressing of copolymerized oligonucleotides and pyrrole, using strands 5'-modified with pyrrole. This direct immobilization method was also used for the production of a DNA biochip. Based on this immobilization method via co-electropolymerization of pyrrole derivatives, microelectrodes modified with polypeptides have also been obtained. This method of immobilization via electro-addressing was also used for creating spots on gold surfaces, for measurements by surface plasmon resonance imaging (SPRi). Thus, pyrazole derivatives of oligonucleotides have been co-electropolymerized at the surface of a gold chip for SPRi of 1 cm². The step of depositing the various sensitive layers is then performed by means of a "pin-electrospotting" system. The same approach was also developed for the immobilization of proteins.

These systems for electro-addressing by "pin-electrospotting" on gold have made it possible to form spots of insoluble films of pyrrole-proteins, pyrrole-oligonucleotides and pyrrole-peptides, making it possible to take SPRi measurements with performance qualities equal to those of standard immobilization systems. A novel method of indirect electro-addressing on gold uses a network of gold electrodes functionalized with a monolayer exposing hydroquinone monoester functions. The grafting of amino-biotin in solution onto these functions is triggered by means of an electro-oxidation. A network of screen-printed electrodes has also been used in order to develop a method for the immobilization of electrochemically addressed proteins. Thus, the palette of sensitive layers that may be obtained by means of electropolymerized films is quite large, and may be applied to the immobilization of proteins, antibodies or oligonucleotides. The biosensors/biochips thus produced also enable both optical and electrochemical detection.

Immobilization by electro-addressing of biomolecules based on the electro-reduction of diazonium salts is, at the present time, scarcely developed. This process is based on the particular grafting properties of the aryldiazonium salts introduced by [Delamar, M. et al., 1992, *Journal of The American Chemical Society*, 114, 5883-5884]:

(a) diazonium salts may be formed from aniline derivatives, in an acidic solution of $NaNO_2$;

(b) this diazonium salt may then be electro-reduced to lead to the release of nitrogen and to the formation of an aryl radical of high reactivity;

(c) this radical becomes grafted onto the surface of the electrode that provided the electron required for its electro-reduction. A covalent bond of C—X type forms, in which X may be gold, cobalt, nickel, zinc, ITO (indium tin oxide film), platinum, copper, graphite, diamond or silicon. Recently, a type of activated layer has been obtained by electrodeposition of diazonium salts premodified with a maleimide group. The layer thus obtained may subsequently be functionalized with biological agents or molecules containing a free thiol function.

The electro-addressing of diazonium salts was used for the first time on glassy carbon electrodes, in order to indirectly immobilize an enzyme. The electro-grafting reaction was then used so as to functionalize the entire glassy carbon surface and thus obtain a layer of phenyl acetate. This method was used to derivatize the surface so as to achieve covalent grafting by chemical coupling of glucose oxidase. This is thus a matter here of an indirect method of electro-addressing. The diazotization reaction on an aniline derivative has also been used in order to graft a biotin monolayer. A biotin-aniline conjugate was then diazotized to form a biotin-aryldiazonium derivative, and then grafted by electro-reduction onto the surface of a screen-printed carbon electrode. Thus, the surface of the electrode becomes a point of covalent attachment for streptavidin. This surface enables the fixing of biotinylated alkaline phosphatase. A direct electro-addressing method for horseradish peroxidase (HRP) has been developed. Coupling between 4-carboxyphenyldiazonium and HRP, via a carbodiimide, is performed, and the HRP-aryldiazonium adept is then electro-addressed onto a glassy carbon electrode. This results in the formation of a sensitive layer of covalently fixed HRP, which enables the detection of hydrogen peroxide by cyclic voltammetry. It may be envisaged to broaden this method to a wider variety of supports, on which it has been shown that aryldiazoniums can be grafted, such as iron, platinum, cobalt, nickel, zinc, copper, gold, ITO and silicon. Recently, a diazonium salt premodified with a maleimide group has been functionalized with a $DNA_{SS}$ [Harper, J. C. et al., 2008, Langmuir, 24, 2206-2211] and then successfully electro-addressed.

The main drawback of immobilizations by adsorption is the virtually systematic and uncontrolled desorption of the biomolecules. The reason for this is that the energies of interaction between the molecules and the support are sensitive to variations in pH and ionic strength of the medium. This phenomenon may arise, for example, during assays performed in complex media such as natural samples.

The covalent immobilization of biological objects or of biologically active molecules proceeds either via activation of a premodified surface, or via modification of the biological object or of the biologically active molecules before its (their) immobilization on the support. These activation steps are generally performed in media that are incompatible with biological media, and result in the formation of side products that may lead to biasing during the measurement. Generally, several expensive purification steps are necessary to obtain an operational biochip. The modification of biological objects or of biologically active molecules may result in a loss of activity of the latter. Furthermore, the modification does not generally take place in a controlled manner and their study remains long and expensive, especially in the presence of a large number of objects to be modified. The type of strategy for the covalent immobilization is also dependent on the substrate or support used for the biochip and for the envisaged detection mode.

There is thus a real need for an efficient method of adhesion between a surface of any type and a species such as another surface, such as that of graphene or of carbon nanotubes, or a molecule such as a molecule that can be used in biosensors, on the basis of bonding of covalent type.

DESCRIPTION OF THE INVENTION

The present invention allows the technical problems and drawbacks listed above to be solved since it concerns finish-coated surfaces, a process for preparing them and their use with any other surface, thus making it possible to achieve adhesion between two materials, one of which has a reactive surface, or between such a reactive surface and molecules of interest in order to immobilize them.

More specifically, the present invention relates to a process for assembling at least one zone of a first surface with at least one zone of a second surface or with a molecule of interest, comprising a step that consists in placing in contact the said zone of the said first surface with the said zone of the said second surface or with the said molecule of interest, the said zone of the said first surface having at least one radical and/or ionic species.

In the context of the present invention, the first surface may be referred to as the "reactive surface". Thus, the terms "first surface" and "reactive surface" are equivalent terms.

In the context of the present invention, the second surface may be referred to as the "coating surface". Thus, the terms "second surface" and "coating surface" are equivalent terms.

For the purposes of the present invention, "assembling" corresponds to a method of chemical assembly of two species, after which the said species are maintained assembled by strong chemical interactions. This assembling or adhesion generally corresponds to the formation of covalent bonds, i.e. the sharing or transfer of electrons between atoms belonging to the two species.

Advantageously, the assembling process according to the invention comprises the following successive steps:

a) optionally, subjecting a zone of the said first surface bearing at least one adhesion primer precursor to conditions that are suitable for obtaining, from the said adhesion primer precursor, at least one adhesion primer, b) subjecting the said zone of the said first surface bearing at least one adhesion primer, optionally obtained in step (a), to non-electrochemical conditions to obtain, on the said zone, at least one radical and/or ionic species;

c) contacting the said zone of the said first surface bearing at least one radical and/or ionic species obtained in step (b) with the said zone of the said second surface or with the said molecule of interest.

The term "molecule of interest" denotes, in the context of the present invention, a molecule, and more particularly a molecule of organic nature, that is capable of reacting with a radical species or with an ionic species. As examples of molecules of interest that can be used in the context of the present invention, mention may be made especially of:

organic molecules comprising weak organic bases such as $CO_2^-$, $SO_3^{2-}$, amines and nitrogenous aromatic molecules;

organic macromolecules such as porphyrins, phthalocyanins and dendrimers;

biological molecules such as peptides, proteins such as enzymes, antibodies or antibody fragments, cell or membrane receptors, polysaccharides, cells or cell parts such as cell organites or cell membranes and nucleic acids such as DNA and RNA. FIG. 2 shows some of these molecules of interest and their use in the context of the process according to the invention;

a hydrophobic molecule as defined hereinafter.

For the purposes of the present invention, the term "surface" should be understood as meaning the outer part of a body or solid support, which limits it in any direction. Insofar as, for the same body (or the same solid support), different surfaces may be defined conceptually, the reactive surface and the coating surface may, of course, belong to the same body (or solid support) or to two different bodies (or solid supports). The invention applies to any type surface irrespective of its geometry. This geometry may be simple, such as a perfectly flat surface, or complex, such as a rough surface, or may bear unblocked cavities, irrespective of the material constituting the surface and the rest of the body or solid support on which it is dependent.

The size of the second surface is variable and may be at the centimetric scale. It generally varies between the micrometric and nanometric scale. Thus, they may be surfaces of bodies of nanometric size, or nano-objects (NB), such as the surface of nanoparticles (NP), of carbon nanotubes (CNT), single-wall carbon nanotubes (SWCNT) or multi-wall carbon nanotubes (MWCNT), flakes of graphene or of silicon nanowires, or surfaces of micrometric size, such as the surface of biochips as used in the industry or of metal particles.

The invention is applicable to a wide variety of surfaces of interest (first and second surfaces) whose composition may be chosen from a wide variety of materials since the process exploits an assembling mechanism of ionic and/or radical nature, generally of radical nature. Thus, the first and second surfaces may be of organic or mineral nature, or of composite nature optionally with a non-uniform composition.

Any surface bearing one or more atom(s) or group(s) of atoms that may be involved in a radical addition or substitution reaction, such as CH, carbonyls (ketone, ester, acid or aldehyde), OH, SH, ethers, amines, halogens, such as F, Cl and Br, is especially concerned by the present invention.

The surfaces of mineral nature may be chosen especially from conductive materials such as metals, noble metals, metal oxides, transition metals, metal alloys, for example Ni, Zn, Au, Pt, Ti or steel. They may also be semiconductive materials, such as Si, SiC, AsGa, Ga, etc. It is also possible to apply the process to non-conductive surfaces such as non-conductive oxides such as $SiO_2$, $Al_2O_3$ and MgO. More generally, a mineral surface may be constituted, for example, by an amorphous material, such as a glass generally containing silicates, or alternatively a ceramic, or equally a crystalline material such as diamond, graphite, which may be more or less organized, for instance graphene or high-organized-phase graphite (HOPG), or carbon nanotubes.

Surfaces of organic nature that may especially be mentioned include natural polymers, such as latex or rubber, or artificial polymers such as polyamide or polyethylene derivatives, especially polymers bearing bonds of n type, such as polymers bearing ethylenic bonds or carbonyl or imine groups. It is also possible to apply the process to more complex organic surfaces such as surfaces comprising polysaccharides, for instance cellulose for wood or paper, artificial or natural fibres, for instance cotton, felt as carbon felt, and also fluorinated polymers such as polytetrafluoroethylene (PTFE), or alternatively to polymers bearing basic groups such as tertiary or secondary amines, for example pyridines, for instance poly-4 and poly-2-vinylpyridines (P4VP and P2VP) or more generally polymers bearing aromatic and nitro-aromatic groups.

Advantageously, the first and second surfaces used in the context of the present invention are constituted of an identical or different material, chosen from the group constituted by metals, metal alloys, wood, paper, cotton, carbon felt, silicon, nanotubes, such as CNTs, graphite materials, for instance coal, graphene, fullerenes and HOPG, organic materials such as organic polymers, fluorinated or non-fluorinated polymers and diamond.

The nature of the first surface, i.e. the reactive surface, has little influence on the process of the invention. Specifically, the presence of a radical and/or ionic species of an adhesion primer or of a precursor of an adhesion primer in the various implementation forms described hereinbelow generally isolates the material constituting this surface from the rest of the system.

It is preferable for the second surface, i.e. the coating surface, to bear at least one atom that can be involved in a radical and/or ionic chemical reaction. Advantageously, the material composing the coating surface will be chosen from materials that are capable of reacting chemically with phenyl radicals or phenyl cations. Mention may be made especially of graphite materials such as HOPG, graphene, CNTs and fullerenes; organic materials, such as organic polymers, such as poly-4-vinylpyridine (P4VP), or polyacrylic acid; and metals and metal alloys; the latter possibly being in the form of metal particles or aggregates.

The zones of the first surface and of the second surface involved in the assembling process according to the invention may be of identical or different size and/or shape. The shape of these zones may be simple or complex. These zones may occupy from 0.01% to 100% of the total surface of the first or second surface. Generally, the zone of the first surface (reactive surface) involved in the assembling is greater than the zone of the second surface (coating surface) involved in the assembling.

In the context of the present invention, the term "adhesion primer" corresponds to any organic molecule that is capable, under certain conditions, of forming either radicals or ions, and more particularly cations, and thus of participating in chemical reactions. Such chemical reactions may especially be chemisorption and particularly chemical grafting.

The term "chemical grafting" refers especially to the use of extremely reactive molecular species (radical or ionic and especially cationic species) that are capable of forming bonds of covalent bonding type with a surface of interest, the said molecular species being generated independently of the surface onto which they are intended to be grafted. Thus, the grafting reaction leads to the formation of covalent bonds between the zone of the coating surface concerned and the adhesion primer derivative.

In the context of the present invention, the term "adhesion primer derivative" means a chemical unit resulting from the adhesion primer, after this primer has reacted with a molecule of interest or by chemical grafting with the coating surface.

The adhesion primer is advantageously a cleavable aryl salt chosen from the group constituted by aryldiazonium salts, aryl ammonium salts, aryl phosphonium salts, aryl iodonium salts and aryl sulfonium salts. In these salts, the aryl group is an aryl group that may be represented by R as defined hereinbelow.

In a first variant of the invention, the adhesion primer is directly bonded to the first surface. In this variant, the adhesion primer is advantageously bonded to the zone of the first surface involved in the assembling process by means of a covalent bond. Thus, this covalent bond bonds an atom of the zone of the first surface involved in the assembling process to an atom of the adhesion primer.

In a second variant of the invention, the adhesion primer is indirectly bonded to the zone of the first surface involved in the assembling process. In this variant, the adhesion primer and the zone of the first surface involved in the assembling process are each bonded to a bonding agent that maintains the bond between the said primer and the said zone. This bonding agent may be in the form of a single species, part of which is bonded to the adhesion primer and another part to the first surface involved in the assembling process. Advantageously, the various bonds involved between the adhesion primer and the bonding agent, on the one hand, and the bonding agent and the zone of the first surface involved in the assembling process, are covalent bonds.

Alternatively, the bonding agent comprises at least two species, which may be identical or different, bonded together, one being bonded to the adhesion primer and the other to the zone of the first surface involved in the assembling process. The bonding agent may bear more than two identical or different species, bonded to each other, the first of these species being bonded to the adhesion primer and the last to the zone of the first surface involved in the assembly process. Advantageously, the various bonds involved between the adhesion primer and one of the species of the bonding agent, between the various species of the bonding agent and between one of the species of the bonding agent and the zone of the first surface involved in the assembling process are covalent bonds. By way of example, the bonding agent may be in the form of a polymer or copolymer, derived from several monomer units of identical or different chemical species.

In this variant, the bonding agent may be in the form of a finish. For the purposes of the present invention, the term "finish" means any film of organic nature, especially derived from several units of organic chemical species, which are preferentially covalently bonded to the zone of the first surface involved in the assembling process according to the invention. They are particularly films covalently bonded to this zone and comprising at least one layer of structural units of similar nature. Depending on the thickness of the film, its cohesion is provided by the covalent bonds that develop between the various units.

This variant especially makes it possible to obtain well-defined localization of the zone of the first surface involved in the process according to the invention.

Specifically, in the context of a conductive or semiconductive surface, the finish may be prepared on a selected zone of this surface according to the following steps:

i) positioning of a microelectrode ME (i.e. an electrode, for which at least one of the characteristic dimensions (the diameter for a disk) is at most of the order of a few tens of micrometers, close to the surface of a selected zone;

ii) placing a liquid solution comprising at least one adhesion primer as defined in the present invention and at least one radical-polymerizable monomer, which is identical to or different from the said adhesion primer, with the said selected zone;

iii) polarization of the said microelectrode and of the surface of the said substrate, the electrical potential of the surface being more cathodic than the reduction potential of the organic adhesion primer used in step (ii).

In general, the sequence of steps is either (i), (ii) and (iii) or (i), (iii) and (ii).

The working distance (i.e. the distance between the ME and the surface of the support) chosen for performing the process is that for which the ratio between the value of the current intensity measured at infinity, i.e. far from the surface, is between 1.2 and 2.5. In general, such a value corresponds to a distance such that the ratio between the working distance and the radius of the ME is between 0.2 and 2.

The radical-polymerizable monomers used in the context of the process for preparing the finish correspond to monomers capable of polymerizing under radical conditions after initiation by a radical chemical entity. Typically, they are molecules comprising at least one bond of ethylenic type. Vinyl monomers, especially the monomers described in patent application FR 05/02516 and in patent FR 03/11491, are particularly concerned.

The radical-polymerizable monomers are advantageously chosen from the group constituted by acrylic acid, vinyl acetate, acrylonitrile, methacrylonitrile, methyl methacrylate, ethyl methacrylate, butyl methacrylate, propyl methacrylate, hydroxyethyl methacrylate, hydroxypropyl methacrylate and glycidyl methacrylate, and derivatives thereof; acrylamides and especially amino-ethyl, propyl, butyl, pentyl and hexyl methacrylamides, cyanoacrylates, diacrylates and dimethacrylates, triacrylates and trimethacrylates, tetraacrylates and tetramethacrylates (such as pentaerythrityl tetramethacrylate), styrene and derivatives thereof, para-chlorostyrene, penta-fluorostyrene, N-vinylpyrrolidone, 4-vinylpyridine, 2-vinylpyridine, vinyl, acryloyl or methacryloyl halides, divinylbenzene (DVB), and more generally vinyl crosslinking agents or crosslinking agents based on acrylate or methacrylate, and derivatives thereof.

The liquid solution comprising at least one adhesion primer and at least one radical-polymerizable monomer may also contain a protic solvent advantageously chosen from the group constituted by water, acetic acid, hydroxylated solvents such as methanol and ethanol, and liquid glycols of low molecular weight such as ethylene glycol, and mixtures thereof.

The liquid solution comprising an adhesion primer and a radical-polymerizable monomer may also contain at least one support electrolyte chosen especially from quaternary ammonium salts such as perchlorates, tosylates, tetrafluoroborates, hexafluorophosphates, short-chain quaternary ammonium halides, sodium nitrate and calcium chloride.

The liquid solution, comprising an adhesion primer and a radical-polymerizable monomer, may also contain at least one surfactant, especially to improve the solubility of the radical-polymerizable monomer. A precise description of the surfactants that may be used in the context of the invention is given in patent application FR 2 897 876, to which a person skilled in the art may refer. A single surfactant or a mixture of several surfactants may be used.

Thus, whether the bonding of the adhesion primer to the zone of the first surface involved in the assembling process is direct or indirect, the adhesion primer is advantageously covalently bonded to the said zone of the first surface.

The cleavable aryl salts beared by the reactive surface (i.e. the cleavable aryl salts covalently bonded to the zone of the first surface involved in the assembling process) are also referred to herein as "supported cleavable aryl salts". Any use herein of the term "supported" corresponds to the above definition.

Among the supported cleavable aryl salts, mention may be made in particular of the compounds of formula (I) below:

(first surface)–(B)$_n$—R—N$_2^+$,A$^-$          (I)

in which:
(B)$_n$ represents a bonding agent,
n is equal to 0 or 1,
A represents a monovalent anion, and
R represents an aryl group.

As defined previously, B may represent a single species, at least two identical or different species, or even a finish as described above.

As aryl groups R that may be used in the context of the present invention, especially for the supported cleavable aryl salts, and more particularly for the compounds of formula (I) above, mention may be made advantageously of optionally monosubstituted or polysubstituted aromatic or heteroaromatic carbon-based structures, constituted of one or more aromatic or heteroaromatic rings each containing from 3 to 8 atoms, the heteroatom(s) possibly being N, O, P or S. The substituent(s) may contain one or more heteroatoms, such as N, O, F, Cl, P, Si, Br or S and also alkyl groups especially of C1-C6.

Within the adhesion primers used in the context of the present invention, especially supported cleavable aryl salts, and more particularly compounds of formula (I) above, the aryl group R is advantageously chosen from aryl groups substituted with electron-withdrawing groups such as NO$_2$, COH, ketones, CN, CO$_2$H, NH$_2$ (in the form of NH$_3^+$), esters and halogens. The aryl groups R that are particularly preferred are nitrophenyl and phenyl radicals.

Within the compounds of formula (I) above, A may be chosen especially from mineral anions such as halides, for instance I$^-$, Br$^-$ and Cl$^-$, halogenoborates such as tetrafluoroborate, perchlorates and sulfonates, and organic anions such as alkoxides and carboxylates.

As adhesion primers that may be used in the context of the present invention, it is particularly advantageous to use a primer chosen from the group constituted by supported phenyldiazonium tetrafluoroborate, supported 4-nitrophenyldiazonium tetrafluoroborate, supported 4-bromophenyldiazonium tetrafluoroborate, supported 4-aminophenyldiazonium chloride, supported 2-methyl-4-chlorophenyldiazonium chloride, supported 4-benzoylbenzenediazonium tetrafluoroborate, supported 4-cyanophenyldiazonium tetrafluoroborate, supported 4-carboxyphenyldiazonium tetrafluoroborate, supported 4-acetamidophenyldiazo ammonium tetrafluoroborate, supported 4-phenylacetic acid diazonium tetrafluoroborate, supported 2-methyl-4-[(2-methylphenyl)diazenyl]benzenediazonium sulfate, supported 9,10-dioxo-9, 10-dihydro-1-anthracenediazonium chloride, supported 4-nitronaphthalenediazonium tetrafluoroborate and supported naphthalenediazonium tetrafluoroborate. Alternatively the counter-ion may be a chloride.

It is clear that the zone of the first surface used in the context of the assembling process according to the present invention may bear several cleavable aryl salts as defined previously, of identical or different nature.

In the context of the present invention, the term "non-electrochemical conditions" means the absence of an external electrical voltage. Thus, the non-electrochemical conditions used in the process according to the invention and especially in step (b) of this process are conditions that allow the formation of radical and/or ionic species from the adhesion primer, in the absence of application of any electrical voltage to the reactive surface. These conditions involve parameters such as, for example, the temperature, the nature of the solvent, the presence of a particular additive, stirring or the pressure, whereas the electrical current does not intervene during the formation of the radical species. Non-electrochemical conditions allowing the formation of radical species are numerous, and this type of reaction is known and has been studied in detail in the prior art (Rempp and Merrill, Polymer Synthesis, 1991, 65-86, Hüthig and Wepf).

It is thus possible, for example, to modify the thermal, kinetic, chemical, photochemical or radiochemical environments of the adhesion primer in order to destabilize it so that it forms a radical and/or ionic species. It is clearly possible to simultaneously modify several of these parameters.

In the context of the present invention, the non-electrochemical conditions allowing the formation of radical and/or ionic species are typically chosen from the group constituted by thermal, kinetic, chemical, photochemical and radiochemical conditions, and combinations thereof. Advantageously, the non-electrochemical conditions are chosen from the group constituted by thermal, chemical, photochemical and radiochemical conditions and combinations with each other and/or with kinetic conditions. The non-electrochemical conditions used in the context of the present invention are more particularly chemical conditions.

The thermal environment depends on the temperature. It is easy to control with the heating means usually used by those skilled in the art. The use of a thermostatically maintained environment is of particular interest since it allows precise control of the reaction conditions.

The kinetic environment corresponds essentially to stirring of the system and to the friction forces. It is not a matter herein of agitation of the molecules themselves (elongation of bonds, etc.), but of the overall displacement of the molecules. The application of a pressure especially makes it possible to supply energy to the system in order for the adhesion primer to be destabilized and to be able to form radical and/or ionic reactive species.

Finally, the action of diverse radiation such as electromagnetic radiation, γ radiation, UV rays or electron or ion beams may also destabilize the adhesion primer sufficiently for it to form radicals and/or ions. The wavelength used will be chosen as a function of the primer used. For example, a wavelength of about 306 nm will be used for supported 4-hexylbenzenediazonium.

In the context of the chemical conditions, one or more chemical initiator(s) is (are) used in the reaction medium. The presence of chemical initiators is often coupled with non-chemical environmental conditions, as outlined above. Typically, a chemical initiator whose stability is lower than that of the adhesion primer under the chosen environmental conditions will evolve into an unstable form that will act on the adhesion primer and will lead to the formation of radical and/or ionic species therefrom. It is also possible to use chemical initiators whose action is not linked essentially to the environmental conditions and which can act over wide ranges of thermal or kinetic conditions. The primer will preferably be suited to the reaction environment, for example to the solvent if a solvent is used.

Many chemical initiators exist. Three types are generally distinguished, as a function of the environmental conditions used:

thermal initiators, the most common of which are peroxides or azo compounds. Under the action of heat, these compounds dissociate into free radicals. In this case, the reaction is performed at a minimum temperature corresponding to that required for the formation of radicals from the initiator. Chemical initiators of this type are generally used specifically within a certain temperature range, as a function of their decomposition kinetic products;

photochemical or radiochemical initiators that are excited by the radiation triggered by irradiation (usually with UV, but also by γ radiation or by electron beams) allow the production of radicals via more or less complex mechanisms. $Bu_3SnH$ and $I_2$ are among the photochemical or radiochemical initiators;

essentially chemical initiators, initiators of this type acting rapidly and under normal temperature and pressure conditions on the adhesion primer to enable it to form radicals and/or ions. Such primers generally have a redox potential that is lower than the reduction potential of the adhesion primer used under the reaction conditions. Depending on the nature of the initiator, it may thus be, for example, a reducing metal, such as iron, zinc or nickel; a metallocene; an organic reducing agent, such as hypophosphorous acid ($H_3PO_2$) or ascorbic acid; an organic or mineral base in proportions that are sufficient to allow destabilization of the adhesion primer. Advantageously, the reducing metal used as chemical initiator is in finely divided form, for instance metal wool (also known more commonly as "straw") or metal filings. Generally, when an organic or mineral base is used as chemical initiator, a pH of greater than or equal to 4 is generally sufficient. Structures of radical reservoir type, for instance polymer matrices irradiated beforehand with a beam of electrons or with a beam of heavy ions and/or with all the irradiation means mentioned previously, may also be used as chemical initiators for destabilizing the adhesion primer and leading to the formation of radical and/or ionic species therefrom.

Depending on the conditions used during step (b) of the process according to the invention, it is clearly possible to use a solvent. Thus, for example, when chemical conditions are used and when a initiator is used, it will advantageously be placed in a solution in contact with the reactive surface to allow destabilization of the adhesion primer and the formation of reactive species. Advantageously, the solvent will be chosen such that it does not significantly react with the reactive surface. Thus, for example, if the adhesion primer is a diazonium salt, it is recommended to use a non-protic solvent.

It is useful to refer to [Chem. Mater. 2007, 19, 6323-6330] for the formation of active species.

The contact of the first surface (reactive surface) with the second surface (coating surface) or with a molecule of interest may be performed, in step (c) of the process of the invention, in different ways.

According to a first embodiment, the placing in contact of step (c) of the process according to the invention is performed directly. Thus, the reactive surface is placed directly in contact with the coating surface or the molecule of interest. For example, a coating surface composed of graphene or of a polymer membrane may be placed directly onto the reactive surface. Similarly, the molecule of interest may be placed directly onto the surface.

According to this embodiment, it is possible to apply a pressure to the coating surface in contact with the reactive surface to destabilize the primer. It is also possible to heat the system, for example to 100° C., or to expose it to illumination, for instance UV illumination in the case of diazonium compounds, particularly when the assembling involves molecules of interest. Example II.1.1 below corresponds to this first embodiment.

According to a second embodiment, the contact of step (c) of the process according to the invention is performed in solution. Generally, the coating surface or the molecule of interest is placed in solution and the solution is then directly contacted with the reactive surface. The solvent of the solution may then be evaporated in order thus to contact directly the coating surface or the molecule with the reactive surface. This embodiment allows wide variability of the coating method (spin coater, dipping, spray, brush, etc.). Examples II.2 below correspond to this embodiment.

Any solvent known to those skilled in the art may be used in this embodiment. A person skilled in the art will know, as a function of the molecule of interest, the coating surface, the radical and/or ionic species and the reactive surface involved, which solvent to use. As examples of solvents that may be used, mention may be made of dimethylformamide and N-methylpyrrolidone.

The immobilization of biological molecules on the zone of the first surface, is advantageously performed in organic medium, in aqueous medium or in buffer medium, which may be, in a non-limiting manner, TRIS buffer (tris(hydroxyethyl) aminomethane), phosphate buffer, acetate buffer, etc. The use of an organic medium is generally preferred for the immobilization of biologically active synthetic products such as, in a non-limiting manner, semi-protected synthetic peptides generally of hydrophobic nature as a result of the protection of the hydrophilic groups, deprotected synthetic peptides that are hydrophobic as a result of a large proportion of amino acids of alkyl or hydrophobic type in the primary sequence of the said peptide, or hydrophobic biological molecules such as, in a non-limiting manner, collagen fibres, transmembrane proteins, and chitin and its derivatives. Typically, the organic solvents used during step (c) involving, as molecules of interest, biological or biologically active molecules, are chosen from the group constituted by acetonitrile, dimethylformamide and dimethyl sulfoxide (DMSO). DMSO will be preferred on account of its low toxicity and its permitted and common use in biology. However, the use of aqueous media or of buffer solutions will be favoured if the molecule to be immobilized shows solubility in these media, even if this solubility is low.

In a first variant of the process of the invention, steps (b) and (c) of the process are performed simultaneously. In this variant, the step corresponding to steps (b) and (c) performed simultaneously consists in concomitantly placing the said zone of the said first surface bearing at least one adhesion primer under non-electrochemical conditions to obtain, on the said zone, at least one radical and/or ionic species and under conditions of contact with the second surface or with the said molecule of interest. The reaction may then be spontaneous or activated.

In this variant, the second surface or the molecule of interest can react directly with the adhesion primer present on the first surface, the second surface and the molecule of interest acting as chemical initiator as defined previously, i.e. a chemical initiator that activates the adhesion primer to give a radical and/or ionic form, and which optionally reacts with this form. Advantageously, in this variant, the coating surface or the molecule of interest is placed in solution as defined previously.

In a second variant of the process of the invention, steps (b) and (c) of the process are not performed, concomitantly. In this variant, it is advantageous, if a reaction solution is used, for this solution to be degassed.

According to one particular embodiment, the process also includes a step of preparing the reactive surface bearing an adhesion primer used in step (b) of the process according to the invention. This additional step corresponds to step (a) of the process according to the invention. The reactive surface bearing an adhesion primer is generally prepared from a surface bearing an adhesion primer precursor. This surface may especially be prepared by coating the first surface, and more particularly the zone of the first surface involved in the assembling, to form thereon a finish comprising an adhesion primer precursor.

In the context of the invention, the term "adhesion primer precursor" should be understood as meaning a molecule that is separated from the adhesion primer via a single operating step that is easy to perform. Generally, the precursors are of higher stability than the adhesion primers under the same environmental conditions. A person skilled in the art knows various "adhesion primer precursor"/"adhesion primer" couples. Thus, for example, arylamines are precursors of aryldiazonium salts. Specifically, via a simple oxidation reaction, for example with $NaNO_2$ in an acidic aqueous medium, or with $NOBF_4$ in organic medium, it is possible to form the corresponding aryldiazonium salts. Under these conditions, passing from a finish comprising a precursor to a finish comprising the corresponding primer is easy. The definition of the term "finish" as given previously for the bonding agent also applies mutatis mutandis to the adhesion primer precursor. Thus, the said zone of the said first surface bearing at least one adhesion primer precursor is a zone of the said first surface to which is bonded, preferentially covalently, an organic film bearing at least one adhesion primer precursor.

Adhesion primer precursors that may especially be mentioned include precursors of supported aryldiazonium salts such as the supported amines of formula (II) below:

(first surface)–$(B)_n$—R—$NH_2$ (II)

in which B, R and n are as defined for formula (I).

As adhesion primer precursors that may be used in the context of the present invention, it is particularly advantageous to use a precursor chosen from the group constituted by supported phenylamine, supported 4-nitrophenylamine, supported 4-bromophenylamine, supported 4-amino phenylamine, supported 2-methyl-4-chlorophenylamine, supported 4-benzylbenzeneamine, supported 4-cyanophenylamine, supported 4-carboxyphenylamine, supported 4-acetamidophenylamine, 4-aminobenzoic acid, supported 2-methyl-4-[(2-methylphenyl)diazenyl]amine, supported 9,10-dioxo-9,10-dihydro-1-anthraceneamine, supported 4-nitronaphthaleneamine and supported naphthaleneamine.

Various coating processes are known in the prior art and may be used according to the nature of the first surface to obtain a surface for which at least one zone bears at least one adhesion primer precursor that can be used in step (a) of the process according to the invention. These processes may be chemical or electrochemical processes. Such processes may, for example, involve dipping, spin-coating, deposition by painting or by spraying, or by pressure and direct contact if the rendering material is solid. Typically, when the user wishes the finish to be covalently bonded to the base surface, the coating operation may be performed via a process of grafting an organic film. Irrespective of the type of surface used, the grafting used may be a chemical grafting as described in [Chem. Mater. 2007, 19, 6323-6330]. When the base surface is conductive or semiconductive, this grafting may advantageously consist of an electro-grafting as described in [*Chem. Mater.* 2006, 18, 4755-4763] or electrografting involving a microelectrode as described previously. The coating process generally leads to the formation of a finish comprising an adhesion primer precursor. Thus, for example, by chemical grafting using aryldiamines, it is possible to form a finish, in this case an organic film, whose surface comprises adhesion primer precursors in the form of supported arylamines.

A person skilled in the art will know how to determine the suitable conditions to be used, during step (a) of the process, as a function of the type of precursor used and of the adhesion primer to be obtained. Thus, the conversion of amine functions into aryldiazonium salts may be performed in a single step using $NaNO_2$ via a simple oxidation reaction, in an acidic aqueous medium, or using $NOBF_4$, in organic medium.

The use of a finish makes it possible especially to precisely select the positioning of the adhesion primer on the surface. Under these conditions, total control of the localization of the surface zones used in the assembling may be obtained. The reason for this is that the coating operation is performed only in the desired zones by the user.

The use of a finish also makes it possible to increase the flatness of the surfaces. Specifically, when the base surface is rough, it is possible to smooth it out by coating with an amount of finish that is large enough to increase the flatness of the surface obtained. The coating operation can, if need be, fill in the unevennesses of the base surface. The invention thus enables the morphology of the reactive surface to be adapted so as to increase the possible contact with the coating surface.

The thickness of the finish may range from a molecular monolayer to a thickness of several nanometers up to the scale of a micron. It is thus possible to modify the electrical conductivity of the finish since, at and above a few nanometers, the organic films become insulating.

Since adhesion primers are particularly reactive molecules, it is possible to conserve the reactive surface more easily when it comprises an adhesion primer precursor rather than an adhesion primer per se.

The adhesion primers, such as the diazonium salts, are the chemical key of the process that enables species such as graphenes to be immobilized on surfaces. The invention makes it possible to achieve chemistry that is difficult to perform with materials of very low reactivity such as graphenes (very thermodynamically stable planar graphite lattice). Graphite materials such as CNTs or fullerenes, which have substantial lattice curvatures, may also be used. Even beyond that, the primers used, such as the diazonium salts, are capable of reacting with a large number of nucleophilic chemical compounds (organic bases $COO^-$, $SO_3^{2-}$, $NH_2$, pyridines, etc.).

The invention differs from the processes of the prior art especially by the fact that, unlike conventional bonding, for which the chemical functions responsible for the adhesion are provided by the adhesive, the chemical functions responsible for the adhesion are already present on the surface, in this case the reactive surface, which may be termed as pre-adhesive.

Furthermore, the process according to the invention may comprise an additional step of structuring of the zone of the first surface used. This structuring consists in modifying the reactive surface, and more particularly in reducing the size of this reactive surface and/or in decreasing the number of radical and/or ionic species on this surface.

Thus, the reactive surface may be subjected to UV irradiation under a UV lamp (spectrum 300-500 nm, 200 W) for a few minutes. Typically, for a 2 nm layer bearing diazonium salts, a UV exposure time of 3 to 10 minutes enables the destruction of all the diazonium salts present on the surface. This result was able to be monitored by IR spectrometry with total disappearance of the peak at 2270 $cm^{-1}$. The layer thus obtained is referred to as the "dead layer" and no longer allows assembling or immobilization of another surface or of a molecule of interest.

The UV irradiation time to obtain the "dead layer" depends on its thickness. As a variant, the irradiation time and/or the irradiation intensity (lower power), the density of the radical and/or ionic species in the zone of the first surface may be controlled, enabling modification of the number of active sites per unit area. This process makes it possible to modify the density of molecules of interest per unit area of the support.

As a variant, the structuring of the zone of the first surface used in the process of the present invention may be performed prior to the preparation of the reactive surface.

This variant may involve either the electro-grafting of a finish using a microelectrode as described previously, or the use of a stamp to be applied to the support.

This stamp, which may be likened to a mask, is applied prior to steps (a) and (b) of the process according to the invention. It typically corresponds to a physical species that is neither grafted to the surface nor covalently bonded thereto. It may especially be a bulk material or a thin layer of material, typically from a few Angstroms to a few microns, generally of organic nature, deposited on the surface.

The stamp enables local "masking" of the chemical reactivity of the surface with regard to the radicals generated during the process and thus leads to controlled formation of a film only on the parts of the surface that are exposed to the solution, the zones of the surface of the support that are equipped with the mask being preserved from the formation of the organic film. The surface of the solid support placed in contact with the liquid solution as defined previously thus typically comprises at least one zone covered with a mask. After removal of the mask at the end of the operation, the surface that was protected, unlike that which was not equipped with a mask, does not comprise any grafted film.

Preferably, the mask will be constituted of a thin layer of mineral or organic material acting as a layer of lower cohesion that can be readily removed under mild conditions. A layer of material is considered as such insofar as it does not require the use of extreme conditions that are harmful to the grafted film in order to be removed. Typically, the mild conditions correspond to simple chemical washing, generally performed using a solvent in which the mask is soluble, ultrasonic treatment in a solvent in which the mask is soluble, or a raising of the temperature. Needless to say, it is desirable for the mask not to be soluble in the solvent present in the liquid solution, i.e. the solvent used in the context of the grafting reaction. Thus, it is recommended to use a mask that has an affinity for the surface higher than that which it has for the reaction solvent.

The material constituting the mask may thus be chosen within a wide range. It will generally be chosen as a function of the nature of the solid support.

The mask may react with the radicals or ions generated during the process. In any case, it is possible to remove it to reveal the zones of the surface of the solid support protected from grafting, on which no organic film will be observed (likened to the "lift-off" methods in lithography).

Mask deposition techniques are well known to those skilled in the art. Such techniques may especially be coating, vaporization or immersion. Thus, the mask, in the form of a thin layer of material, may be deposited, for example, either by direct drawing using a felt (pencil type) impregnated with the chosen material. On glass, it is possible, for example, to use, as mask, a marker such as those sold in stationery shops, or alternatively greasy substances like wax. It is also possible to use the "stamping" process. This technique is applicable especially in the case of a solid support having a surface that is complexing for sulfur atoms, for instance a gold surface; in this case, the mask will generally be composed of alkylthiols, in particular long-chain alkylthiols, usually of C15-C20 and typically of C18 (technique known as "microcontact printing"). More generally, standard lithography techniques may be used to form the mask: spin-coating, followed by exposure through a physical mask or via a beam of light or of guidable particles, and then revelation.

The present invention finds particularly advantageous applications in the field of biology. Specifically, the support used in the context of the present invention may be in various forms, of variable size and useful in biology. As non-exhaustive examples, it may be in the form of slides, microplates, especially 12-, 24- or 96-well microplates, particles, beads, microbeads, fibres, felts, tubes such as haemolysis or microchannel tubes of capillary type, columns or microcolumns such as SPIN™ columns, and supports used for biosensors or biochips. These various types of support may have sizes ranging from a few hundred micrometers to several centimeters. In these applications in biology, the molecules of interest to be assembled or immobilized, which are referred to hereinbelow as "biological or biologically active molecules", will advantageously be chosen from the group constituted by peptides; proteins such as gelatin, protein A, protein G, streptavidin, biotin or an enzyme; antibodies or antibody fragments; cell or membrane receptors; polysaccharides such as glycoaminoglycans and especially heparin; cells or cell parts such as cell organites or membranes, and nucleic acids such as DNA and RNA.

Thus, as explained previously, the present invention may be used for the preparation of biochips or biosensors. This preparation may have different embodiments:

a layer of an adhesion primer precursor of the diazonium type is formed on a conductive or insulating support, of organic or mineral nature, and the layer is activated to form radical and/or ionic species, and then:
the biological or biologically active molecule is deposited on the total surface of the support, or
the biological or biologically active molecule is deposited by means of a micro- or nano-fluidic system directly or sequentially in the form of a drop, another molecule thus being able to be introduced by means of the deposition of a drop, and so on, or the activated support is dipped in the solution containing the biological molecule or the biologically active molecule.

An example of an adhesion primer precursor of the diazonium type is especially a compound of polyphenyl structure.

It is possible, for all the variants defined previously, to perform a step of structuring of the surface of the support used in the process according to the invention.

This structuring may consist of an intermediate step with the deposition of a mask followed by UV irradiation, before the deposition or immobilization of the biological molecule or the biologically active molecule. Thus, a grid or a mask deposited on the activated support, having a particular geometry, allows a spot to be obtained (square, circle, etc.) and the assembly is then subjected to UV irradiation for a predefined time. The zones of the UV-irradiated adhesion primer will then be considered as inactive. The zones of the adhesion primer that have not been UV-irradiated will still be considered as active. They will preferentially be located at the surface of the spots that it is desired to create.

One variant of this structuring may consist, prior to the implementation of the process according to the present invention, in using a pad that serves to mask certain zones of the surface as defined previously.

For all the variants defined previously, it is possible to obtain the layer of adhesion primer precursor of the diazonium type:
- by forming a layer of such a precursor electrochemically on a conductive or insulating support, and especially as described in international patent application WO 2008/078 052, the support possibly being of organic or mineral nature;
- a deposit in the form of drops containing the chemically activated diamine on a conductive or insulating support of organic or mineral nature, creating patterning via a nano- or micro-fluidic system and thus a spot of precursor of an adhesion primer of the diazonium type;
- a deposit in the form of drops containing the electrochemically activated diamine with a nano- or micro-fluidic system with a counter-electrode on a conductive support of organic or mineral nature, creating patterning via a nano- or micro-fluidic system and thus a spot of precursor of an adhesion primer of the diazonium type;
- the direct formation of a layer of diazonium on a chip (which has surface structuring in spots, for example) via an electrochemical process, each of the metal spots of the chip being covered with a layer of diazonium. Each metal spot is then covered with a drop of a defined volume containing the biological molecule(s) of interest.

The present invention also relates to a solid support whose surface bears at least one zone as defined previously, i.e. a zone with at least one radical and/or ionic species, with at least one adhesion primer, or with at least one adhesion primer precursor. The said species, primer and precursor may be directly or indirectly bonded to the said surface, and this may take place in the various embodiments previously envisaged. Everything that has been defined previously regarding the surface (shape, nature, size, etc.) applies mutatis mutandis to the present solid support.

The present invention also relates to the use of a solid support as defined previously for preparing a biochip or a biosensor, and to a biochip or a biosensor comprising a solid support, the surface of which bears at least one zone with at least one radical and/or ionic species as defined previously that has reacted with a biological component chosen from the group constituted by peptides; proteins such as gelatin, protein A, protein G, streptavidin, biotin or an enzyme; antibodies and antibody fragments; cell or membrane receptors; polysaccharides such as glycosaminoglycans and especially heparin; cells or cell parts such as cell organites or membranes, and nucleic acids such as DNA and RNA.

The present invention also relates to a kit of components that can be used during the implementation of a process as defined previously. Such a kit especially comprises:
- in a first compartment, a solid support, the surface of which bears at least one zone as defined previously, i.e. a zone with at least one radical and/or ionic species, with at least one adhesion primer, or with at least one adhesion primer precursor;
- optionally, in a second compartment, at least one component necessary for producing the adhesion primer from its precursor (for example a solution of $NaNO_2$ in an acidic aqueous medium, or a solution of $NOBF_4$, in organic medium) and/or at least one component necessary for producing a radical and/or ionic species from the adhesion primer, such as a chemical initiator;
- optionally, in a third compartment, another solid support or a nano-object whose surface corresponds to the second surface as defined previously or a molecule of interest as defined previously, to be immobilized.

The present invention also relates to the use of a solid support, at least one zone of the surface of which comprises at least one radical and/or ionic species, for immobilizing thereon another solid support or a nano-object whose surface corresponds to the second surface as defined previously. Thus, the present invention relates to the use of a solid support, at least one zone of the surface of which comprises at least one radical and/or ionic species, for immobilizing thereon a single-wall or multi-wall carbon nanotube, a graphene flake or a silicon nanofilm.

More particularly, the present invention relates to the use of a process as described previously or of a solid support, at least one zone of the surface of which comprises at least one radical and/or ionic species as defined, for exfoliating graphene flakes.

Furthermore, the present invention relates to the use of a process as described previously or of a solid support, at least one zone of the surface of which comprises at least one radical and/or ionic species as defined, for metallizing a zone of the said first surface. Specifically, when the second surface used is a nano-object (NB) and especially a nanoparticle (NP), it is possible to use a solution comprising one or more metal salts that can be reduced by the NB immobilized on the first surface after implementation of the process according to the invention. In general, the support on which the NB is immobilized will be directly immersed into a solution comprising one or more metal salts that can be reduced by the NB.

The present invention also finds a use in the field of surfaces treatment. Specifically, it may be used for durably treating a material and especially for modifying the properties such as the surface energy, also known as the "surface tension", the "superficial tension", the "interface energy" or the "interface tension", of at least one of its surfaces and thus for modifying the wettability of this surface. The invention makes it possible especially to modify the interface properties between the said material and a liquid.

In the context of the present invention, the expression "modifying the surface energy" means either increasing or decreasing the surface energy, especially relative to a given liquid, whether it is hydrophilic or hydrophobic. The process according to the present invention makes it possible to modify (i.e. to increase or decrease) the contact angle of a liquid placed on the surface thus treated relative to the contact angle of the same liquid placed on the said untreated surface. Advantageously, the process according to the present invention is a process that makes it possible to modify (i.e. to increase or decrease) the wettability of the said surface.

In this application, the surface whose surface energy it is desired to modify is a "reactive surface" as defined previously. It may be of any nature previously envisaged (organic, mineral, insulating, conductive or semiconductive). More particularly, this surface is a glass surface such as a flat glass used especially in the building industry, architecture, motor vehicles, glazing and mirror-making, an aquarium glass, an eyeglass or an optical glass. In addition, the thickness of the organic coating on the reactive surface assembled with the molecule of interest is easily controllable, which does not modify the optical properties of the material.

The hydrophobic molecules are typically insoluble in protic solvents and particularly in water. The solubility of these molecules is finite and they may form phases that are immiscible with protic solvents such as water. They generally comprise at least one chemical group that is termed hydrophobic. The hydrophobic group participates in modifying the surface energy. The hydrophobic group is advantageously chosen from the group constituted by:

- a linear, branched or cyclic C3 to C50, especially C6 to C30 and in particular C10 to C20 alkyl that may optionally comprise at least one unsaturation (double or triple bond), at least one heteroatom and/or at least one substitution,
- a C3 to C50, especially C6 to C30 and in particular C10 to C20 aryl that may optionally comprise at least one substitution, such substitution may be a linear, branched or cyclic C3 to C50, especially C6 to C30 and in particular C10 to C20 alkyl that may optionally comprise at least one unsaturation (double or triple bond) and/or at least one heteroatom,
- a C6 to C50, especially C6 to C30 and in particular C10 to C20 (poly)cycle that may optionally comprise at least one unsaturation (double or triple bond), at least one heteroatom and/or at least one substitution.

The said substitution is advantageously a substitution with a C1 to C6 alkyl and/or with a halogen and especially a fluorine.

A molecule of interest that may be used for this application is especially a surfactant, and in particular a fluorinated surfactant such as those contained in the compositions sold by DuPont under the brand name Zonyl.

The present invention thus relates to a process for modifying the surface energy of at least one surface of a solid, which consists in assembling the said surface with a hydrophobic molecule as defined previously, according to an assembling process as defined previously.

Advantageously, this process of modifying the surface energy comprises an additional step, following this assembling, which consists in subjecting the said surface assembled with the said molecule to a heat treatment. Specifically, this heat treatment makes it possible to improve the modification of the surface energy. The said heat treatment consists in subjecting the said grafted film to a temperature that may be chosen between 60 and 180° C., especially between 90 and 150° C. and in particular of about 120° C. (i.e. 120° C.±10° C.), for a time generally of between 1 hour and 3 days, especially between 6 hours and 2 days and in particular between 12 and 24 hours. This heat treatment step may be performed in a drying kiln or in an oven.

Other characteristics and advantages of the present invention will emerge more clearly on reading the examples below, which are given as non-limiting illustrations, and with reference to the attached figures.

BRIEF DESCRIPTION OF THE DRAWINGS

FIGS. 8A, 8B, 8C and 8D represent different zones at different magnifications.

FIGS. 9A, 9B, 9C and 9D correspond to different magnifications of the grafting surface, respectively 80 000×, 20 000×, 50 00× and 35000×.

DETAILED DESCRIPTION OF PARTICULAR EMBODIMENTS

The examples that follow were performed, unless otherwise mentioned, under normal temperature and pressure conditions (about 25° C. at about 1 atm) in ambient air. Unless otherwise mentioned, the reagents used were obtained directly commercially, without further purification. The reactions were performed using 7.5×1.2 cm microscope slides (glass slides) covered by evaporation under vacuum with 5 nm of chromium and then 200 nm of gold).

No precautions were taken concerning the composition of the atmosphere, and the solutions were not degassed.

I-Preparation of the First Surface
I-1 Preparation of the Adhesion Primer Precursor
I-1-1 Chemical Protocol The finish was prepared according to the protocol illustrated in [Chem. Mater. 2007, 19, 6323-6330].

Figure 1:
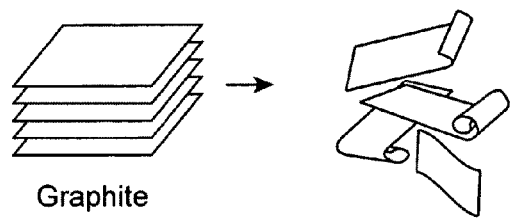
FIG. 1 is a schematic representation of the exfoliation of graphene.
Figure 2:
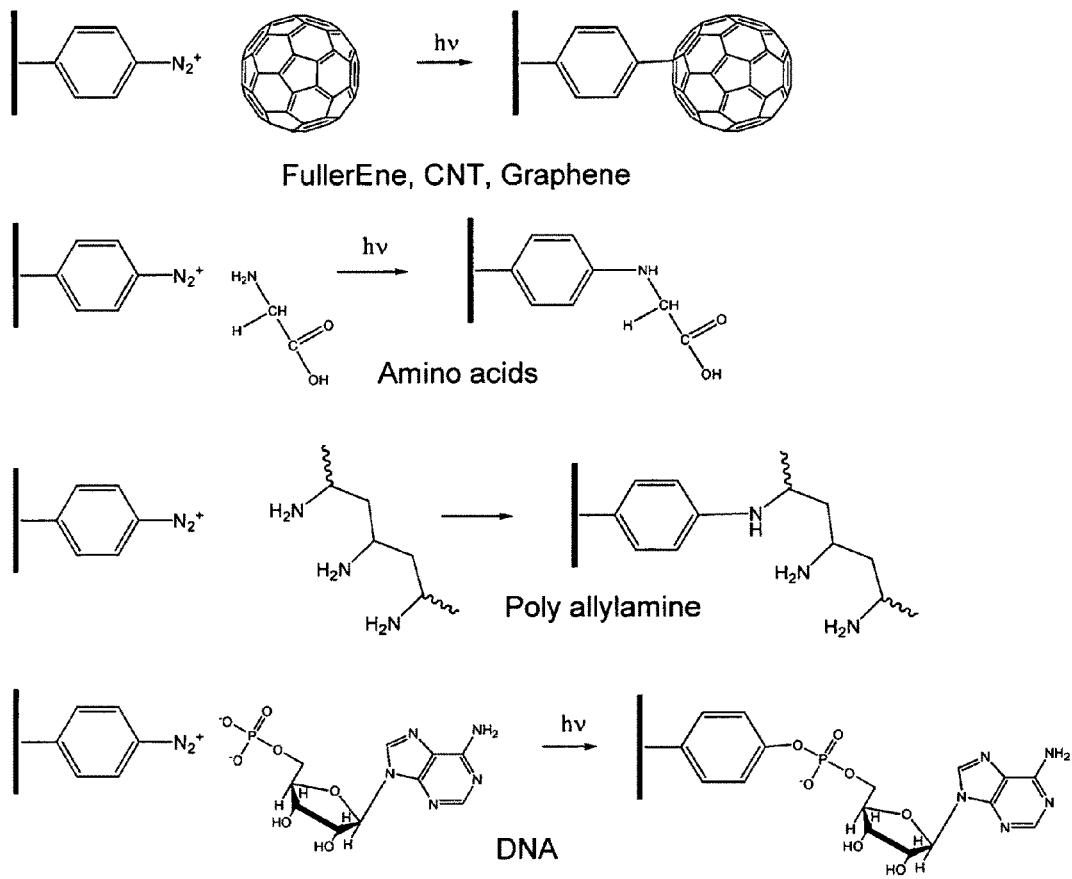
FIG. 2 shows examples of chemical reactions creating a covalent bond between the adhesion primer and the coating.
Figure 3:
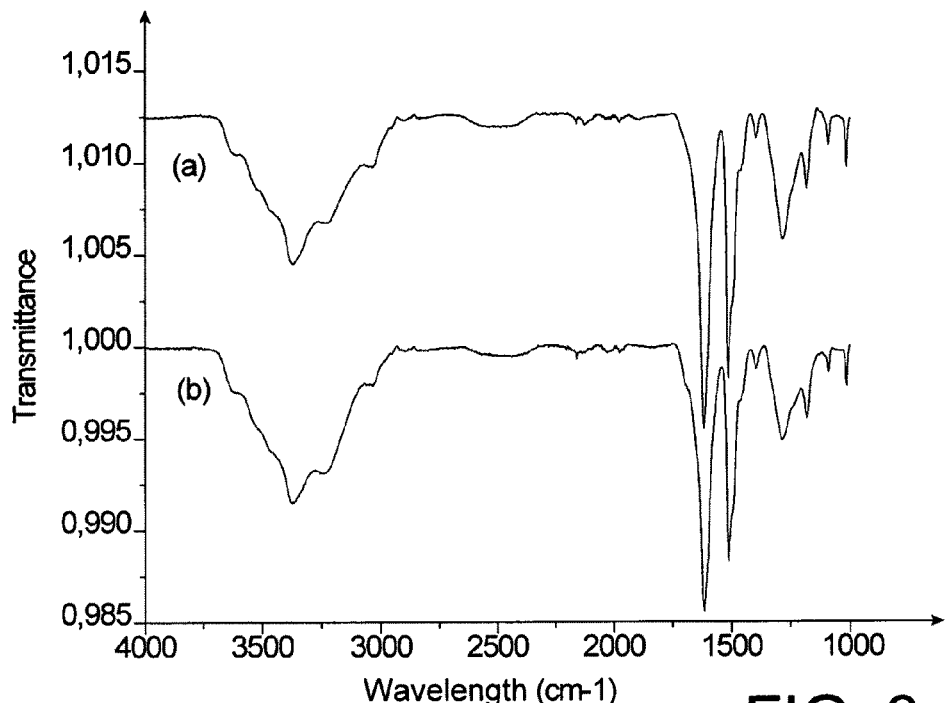
FIG. 3 shows the ATR-IR spectrum of the film of chemically deposited adhesion primer precursor, 40 minutes (polyaminophenylene type): before (a) and after (b) rinsing with water followed by 5 minutes of ultrasonication in acetone.

Microscope slides were immersed for 40 minutes in a mixture comprising 2 ml of aqueous $NH_2$-Ph-$NH_2$ solution ($5\times10^{-3}$ M in 0.5 M HCl), 2 ml of aqueous $NaNO_2$ solution ($5\times10^{-3}$ M) and 80 mg of iron filings. In contrast with the protocol of Chem. Mater. 2007, 19, 6323-6330, the reaction is performed here at 35° C. in order to obtain thicker films. The infrared (IR) spectrum of the sample, analysed after 40 minutes of reaction, is shown in FIG. 3.

The resistance to ultrasonication of the layer formed was tested successfully in acetonitrile. The infrared spectra acquired before and after ultrasonication (spectra (a) and (b), respectively, FIG. 3) are similar and consequently indicate that there was no loss of material and that the film is solidly grafted.

Strips of polyvinylidene chloride (PVDF) β (1 cm×4 cm and 25 µm thick) membranes were dipped for 120 minutes in a mixture comprising 2 ml of aqueous $NH_2$-Ph-$NH_2$ solution ($5\times10^{-3}$ M in 0.5 M HCl), 2 ml of aqueous $NaNO_2$ solution ($5\times10^{-3}$ M) and 80 mg of iron filings. In contrast with the protocol of Chem. Mater. 2007, 19, 6323-6330, the reaction is performed here at 35° C. in order to obtain thicker films.

I-1-2 Electrochemical Protocol

The electrochemical protocol that was used is similar to the one described in [*Chem. Mater.* 2006, 18, 4755-4763]. The reaction was performed in an electrochemical cell containing 10 ml of an electrochemical solution corresponding to an aqueous solution of 1,4-phenylenediamine ($10^{-2}$ M) and $NaNO_2$ ($5\times10^{-3}$ M) in 0.5 M HCl.

The deposition of the films was performed potentiostatically (the chosen potential being within the electroactivity barrier of the diazonium salt) or potentiodynamically (cyclic voltammetry) with a sweep rate of 20 mV·$s^{-1}$.

Figure 4:
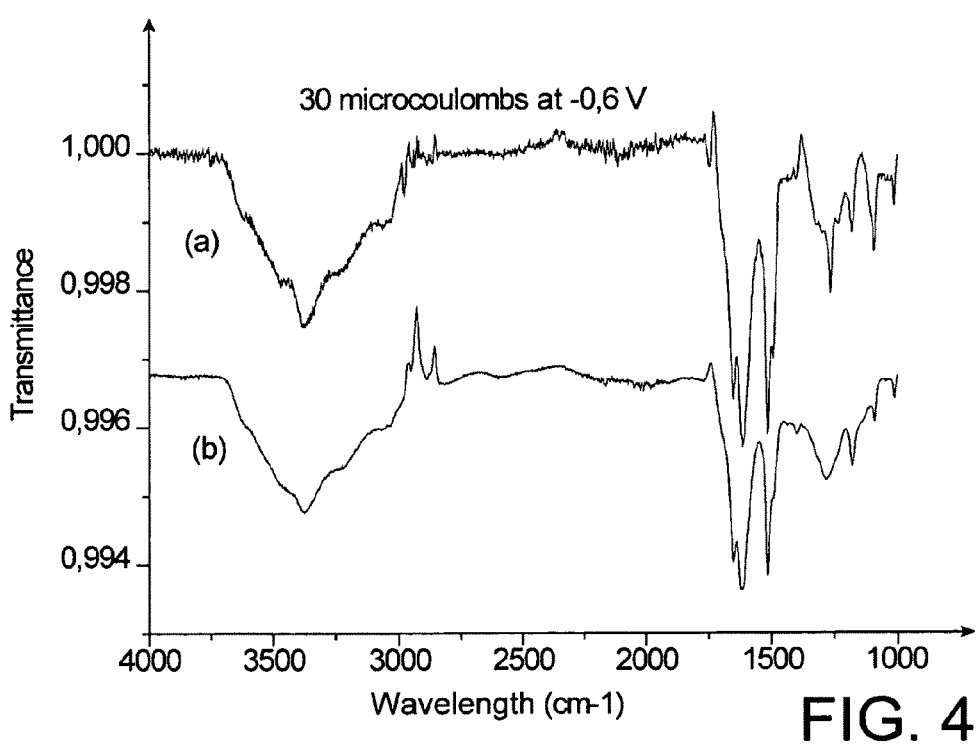
FIG. 4 shows the ATR-IR spectrum of the film of electrochemically deposited adhesion primer, 30 mCb at −0.6 V (polyaminophenylene type): before (a) and after (b) rinsing with water followed by 5 minutes of ultrasonication in acetone.

The IR spectra of the films obtained before and after ultrasonication in acetonitrile (spectra (a) and (b), respectively, FIG. 4) are similar. There was therefore no loss of matter, and the film that was formed is solidly grafted.

I-2 Formation of the Adhesion Primer

The substrates coated with the finish (chemical and electrochemical), obtained in I-1, may be treated in organic medium or in aqueous medium to create a diazonium function.

I-2-1 Organic Medium

The surfaces coated with the finish (aromatic amine form of chemical or electrochemical origin) were immersed in an acetonitrile solution containing $NOBF_4$ ($10^{-2}$ M) for 30 seconds. During this step, the $NOBF_4$ concentration does not need to be precise, since there is always an excess relative to the amine functions present at the surface.

Figure 5:
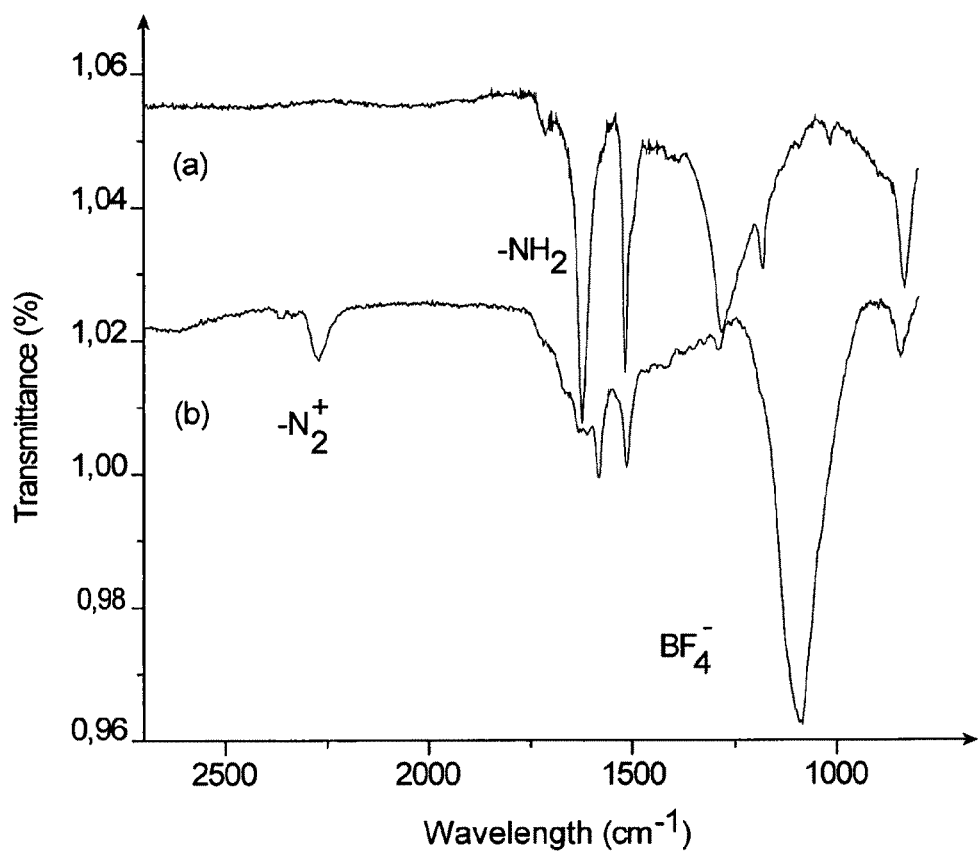
FIG. 5 shows the IR spectrum (a) of a surface coated with a thin layer of aromatic amines, referred to as the chemically prepared adhesion primer precursor surface, (b) of the same surface that has become the adhesion primer after treatment with $NOBF_4$ ($10^{-2}$ M) for 30 seconds in $CH_3CN$.
Figure 6:
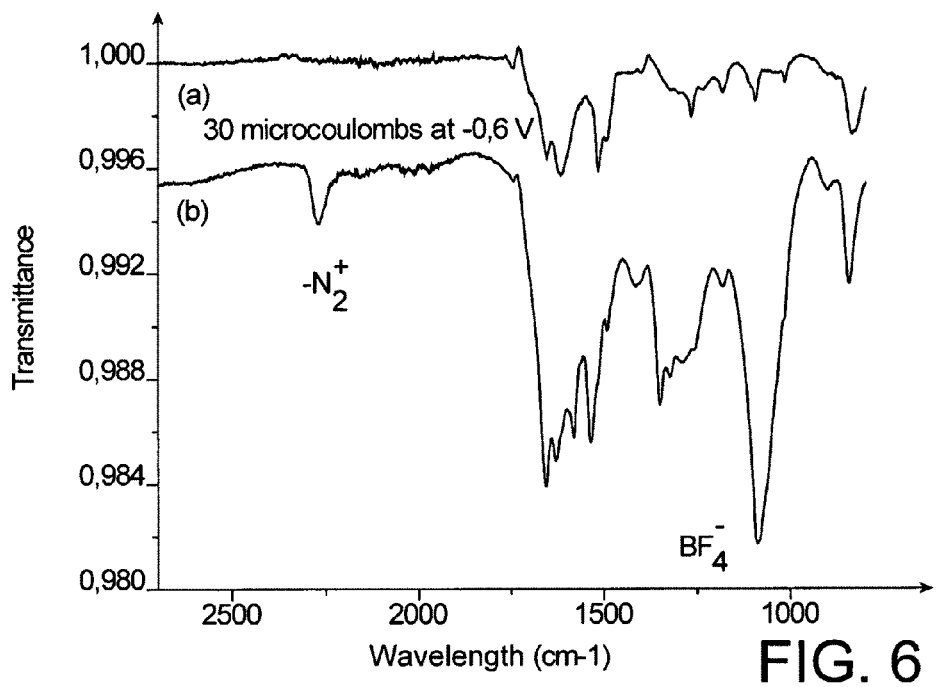
FIG. 6 shows IR spectra (a) of a surface coated with a thin layer of aromatic amine, this surface being referred to as the electrochemically prepared adhesion primer precursor, and (b) of the same surface that has become the adhesion primer after treatment with $NOBF_4$ ($10^{-2}$ M) for 30 seconds in $CH_3CN$.

The formation of the diazonium salts was able to be monitored by infrared spectrometry: a peak at 2270 $cm^{-1}$ corresponding to the diazonium and a peak at 1080 $cm^{-1}$ corresponding to its counterion $BF_4^-$ appear as illustrated in FIG. 5 for a film of chemical origin (I-1-1), and FIG. 6 for a film of electrochemical origin (I-1-2).

The reaction performed in Example I-2-1 may be represented schematically in the following manner:

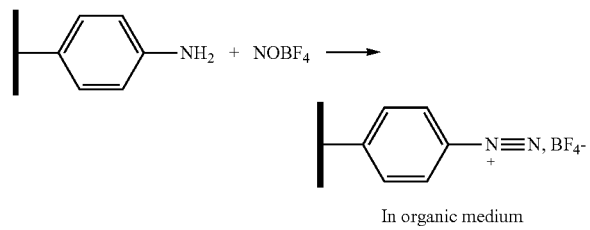

I-2-2 Aqueous Medium

The surfaces coated with the finish were immersed in an aqueous solution of 0.5 M HCl and $5\times10^{-2}$ M $NaNO_2$. During this step, the $NaNO_2$ concentration does not need to be precise, since there is always an excess relative to the amine functions present at the surface.

Figure 7:
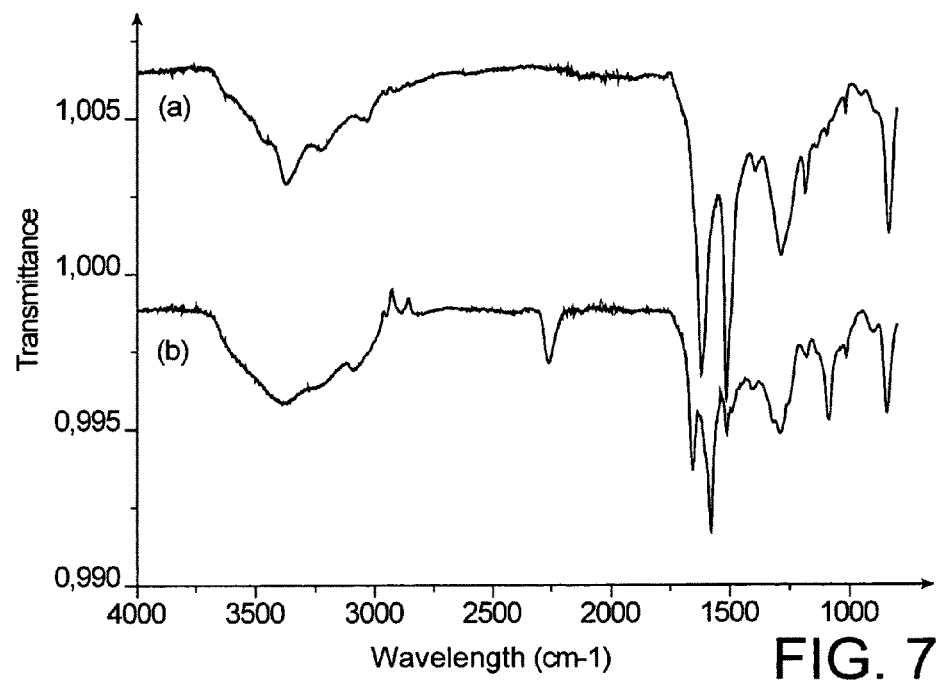
FIG. 7 shows the re-diazotization in aqueous medium (thus absence of the $BF_4^-$ band): (a) IR spectrum of the precursor surface, (b) IR spectrum of the primer surface.

The formation of the diazonium salts was able to be monitored by IR spectrometry: a peak at 2270 $cm^{-1}$ corresponding to the diazonium as illustrated in FIG. 7. The reaction performed in Example I-2-2 may be represented schematically in the following manner:

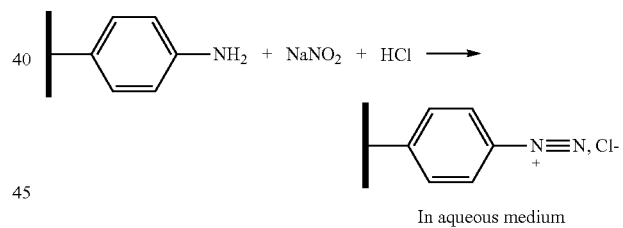

I-3 Structuring of the Surface or "Patterning"

Some of the surfaces obtained after the treatments described in paragraph I-2 are covered with a mask. The mask is in the form of a glass plate lithographically treated with an opaque metal. The surface bearing the lithographically produced patterns is placed directly in contact with the activated cell-adhesive layer and the assembly was subjected to UV irradiation under a UV lamp (spectrum 300-500 nm) for a few minutes.

The appearance of "patterning" on the surface of the support containing "dead" parts and of activated self-adhesive spots was able to be revealed by IR spectrometry mapping, with the appearance of a peak at 2270 $cm^{-1}$ for the zones protected with a mask, and disappearance of the peak at 2270 $cm^{-1}$ for the UV-irradiated zones.

Certain surfaces of gold slides are covered with a mask made using a marker such as those sold in stationery shops. After the treatments described in paragraph I-2, the appearance of "patterning" at the surface of the support containing bare parts and of activated self-adhesive spots was able to be revealed by IR spectrometry mapping, with the appearance of a peak at 2270 cm$^{-1}$ for the zones not protected with the mask, and disappearance of the peak at 2270 cm$^{-1}$ for the zones covered with markers.

II-Assembly/Immobilization

II-1 Immobilization of Mineral Materials

II-1-1 Graphene by Exfoliation of HOPG

A block of HOPG (obtained from Advanced Ceramics Corporation, ZYH grade, 12×12×2 mm in size) deposited on an adhesive tape (sold by 3M, Scotch Magic™ 810 invisible) was placed in contact with the surfaces obtained in Examples I-2. A pressure, of between 0.1 and 10 bar, was exerted, using a drill press vice and the assembly was placed in an oven at 100° C. for one hour.

Figure 8:
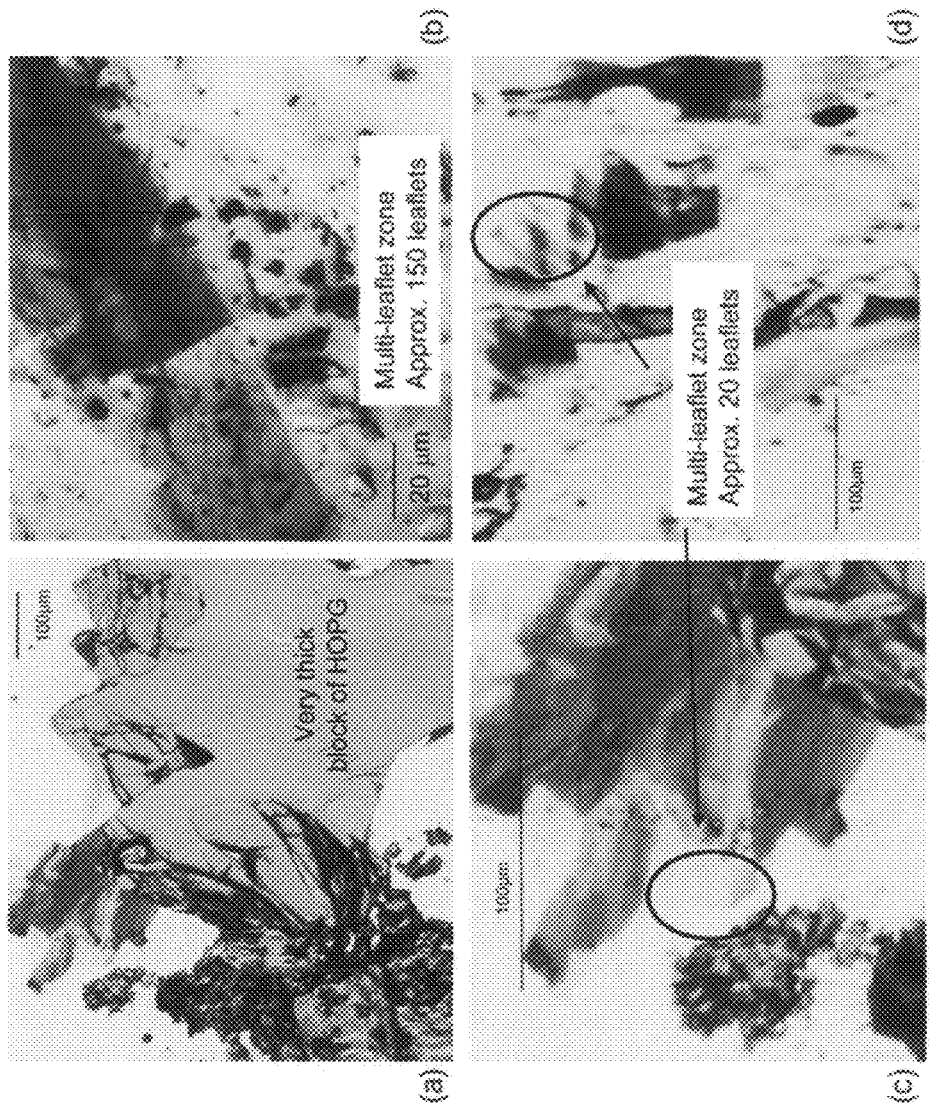
FIG. 8 shows the grafting of graphene multi-flakes onto a diazotized surface.
Figure 9:
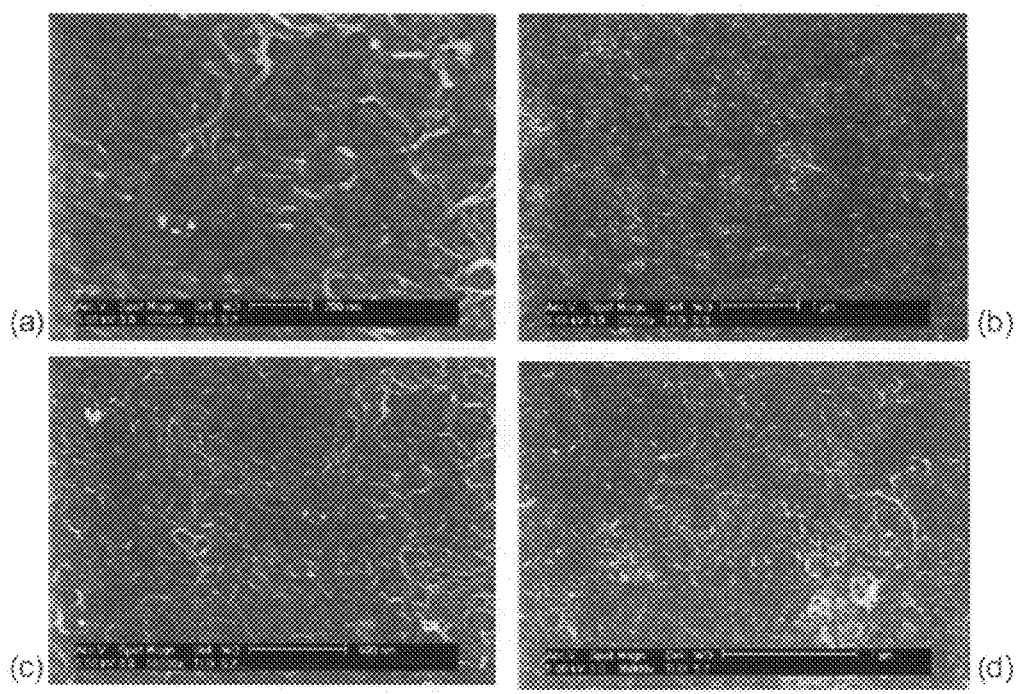
FIG. 9 shows the grafting of CNT onto a diazotized surface.

After this treatment, the graphene flake of the block of HOPG directly in contact with the adhesion primer is grafted. The grafted block has a thickness of about 50 nm, i.e. amount 150 graphene flakes (FIG. 8B).

The exact characterization of the mono-flake requires a Raman analysis that is difficult to perform on certain zones that appear diffuse (FIGS. 8C and 8D): a number of flakes of less than 20 is definitely obtained. The block of grafted HOPG withstood ultrasonication (FIG. 8A).

II-1-2 Carbon Nanotubes (CNT)

Multi-wall carbon nanotubes (MWCNTs) with an outside diameter of between 4 and 15 nm (synthesized by CCVD, very pure, sold by the company Nanocyl) were added at a rate of 0.3 mg/ml to N-methylpyrrolidone and then exposed to ultrasonication for 6 hours to give a stable dispersion.

Centrifugation at 7000 rpm allowed separation of the poorly dispersed CNTs. 10 ml of supernatant were taken, and a gold covered microscope slide, prepared according to protocol I-2, was immersed therein. The reaction medium was maintained at 100° C. with stirring. After 12 hours, the slide was removed and then rinsed thoroughly with ethanol and acetone.

The surfaces thus treated were analysed by scanning electron microscopy: the uniform deposit of CNT observed at different magnifications is shown in FIGS. 9A, 9B, 9C and 9D.

II-1-3 Copper Nanoparticles

Copper nanoparticles were prepared according to the following manner: to a beaker containing 50 ml of aqueous CuSO$_4$ solution (250 mg CuSO$_4$.5H$_2$O, copper sulfate pentahydrate, in 50 ml of deionized water), were added 2 g of surfactant HEA$_{16}$Cl [N,N-diméthyl-N-cetyl-N-(2-hydroxyethyl)ammonium chloride] with magnetic stirring for several minutes (typically from 2 to 10 minutes). Next, 2 ml of an NaBH$_4$ solution were introduced into the beaker. The NaBH$_4$ solution was prepared by dissolving 150 mg of NaBH$_4$ in 2 ml of deionized water. Stirring was stopped when a blue-black coloration appeared (typically 1 to 5 minutes). The solution then turned a red-black colour in 5 to 10 minutes.

The surface coated with the diazonium salts was then dipped in the solution, typically for between 5 and 30 seconds. Longer times allowed more complete covering. The samples were then rinsed with deionized water. Blank reference surfaces simply coated with polyphenyleneamine were also soaked under the same conditions to evaluate the spontaneous adsorption of the nanoparticles onto these surfaces.

The images of these various surfaces obtained by scanning electron microscopy revealed the presence of dendritic copper only on the surface coated with the diazonium salts, and not on the reference surfaces.

II-2 Immobilization of Organic Compounds

II-2-1 Simple Organic Compounds: acetylpyridine, 4-vinylpyridine, ethyl 4-pyridylacetate Microscope slides comprising an adhesion primer prepared, according to the protocols outlined in I-2, were used.

Figure 10:
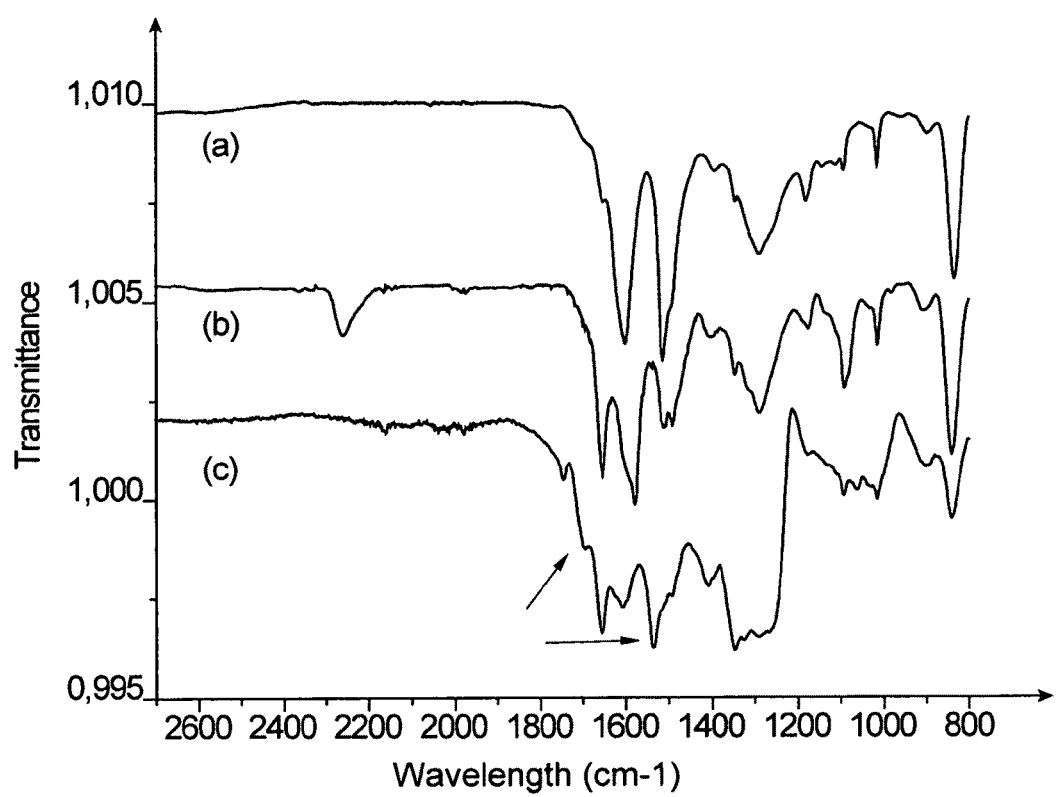
FIG. 10 shows the IR spectrum of a surface coated with a primer precursor of polyaminophenylene type (a), of a primer (b) and after reaction with acetylpyridine (c).
Figure 11:
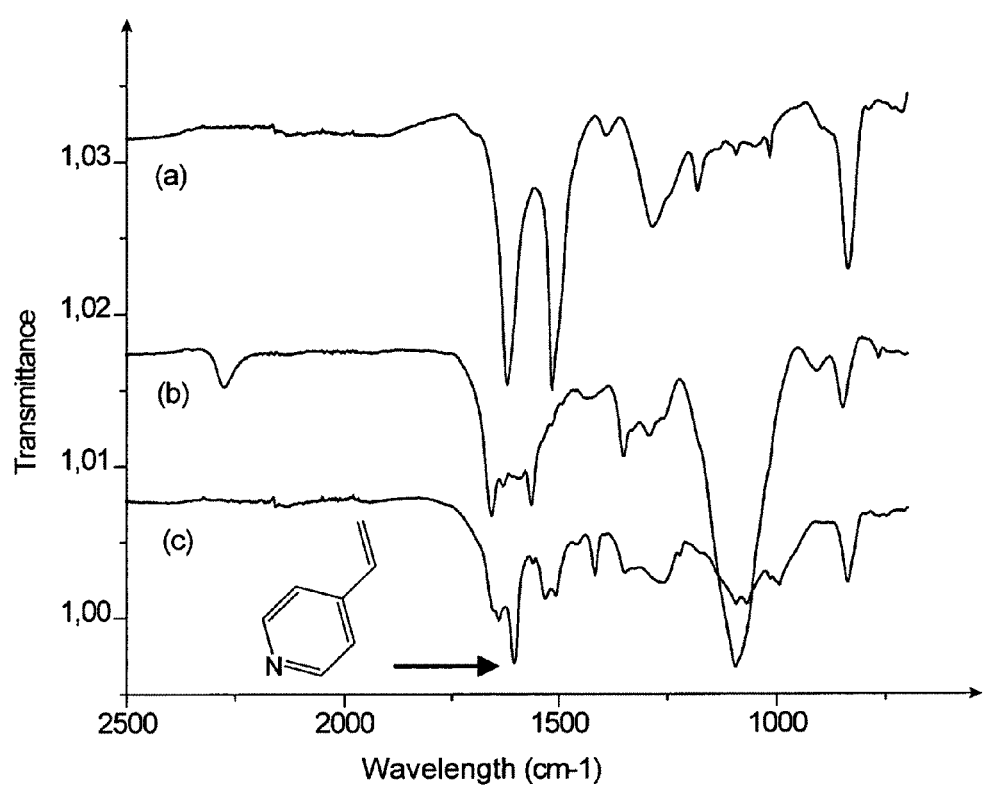
FIG. 11 shows the IR spectrum of a surface coated with a primer precursor of polyaminophenylene type (a), and of a primer (b) and after reaction with 4-vinylpyridine (4VP) (c).
Figure 12:
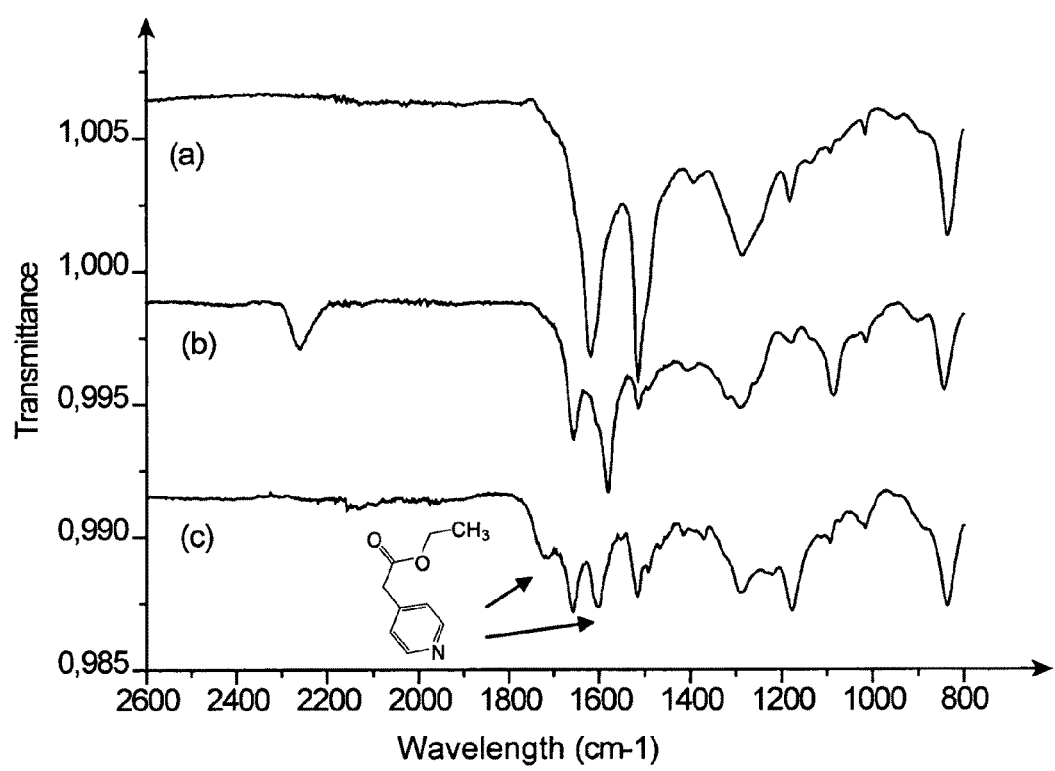
FIG. 12 shows the IR spectrum of a surface coated with a primer precursor of polyaminophenylene type (a), and of a primer (b) and after reaction with ethyl 4-pyridylacetate (c).

The samples were immersed for 3 minutes in a solution of acetylpyridine, 4-vinylpyridine or ethyl 4-pyridylacetate. After rinsing with dimethylformamide (DMF) and exposure to ultrasound, the surfaces were analysed by IR spectrometry: the spectra are presented in FIGS. 10 (acetylpyridine), 11 (4-vinylpyridine) and 12 (ethyl 4-pyridylacetate).

The reaction performed in Example II.2.1 with 4-vinylpyridine is probably as follows:

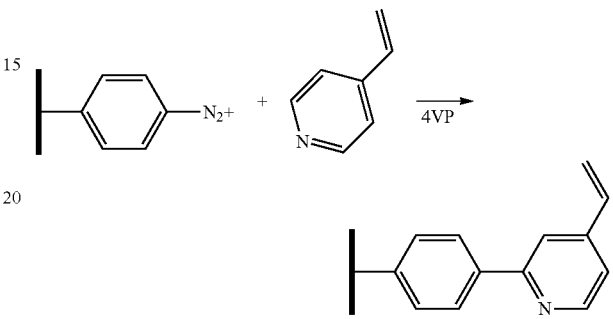

II-2-2 Polymer: Poly-4-vinylpyridine

Microscope slides comprising an adhesion primer, prepared according to the protocols outlined in I-2, were used.

Poly-4-vinylpyridine (P4VP) was dissolved to a proportion of 2% by mass in dimethylformamide (DMF) to achieve good dispersion. The microscope slide was placed on a spin coater and covered with the P4VP solution. Spinning at 2000 rpm (revolutions per minute) for one minute makes it possible to form a thin film of P4VP. 5 minutes after deposition, the slide was rinsed and exposed to ultrasound in DMF.

The reaction performed in Example II.2.2 is is probably as follows:

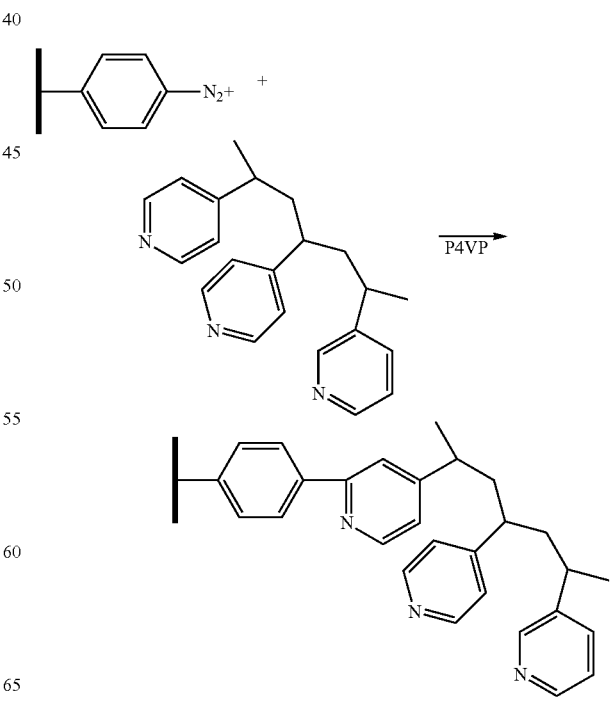

Figure 13:
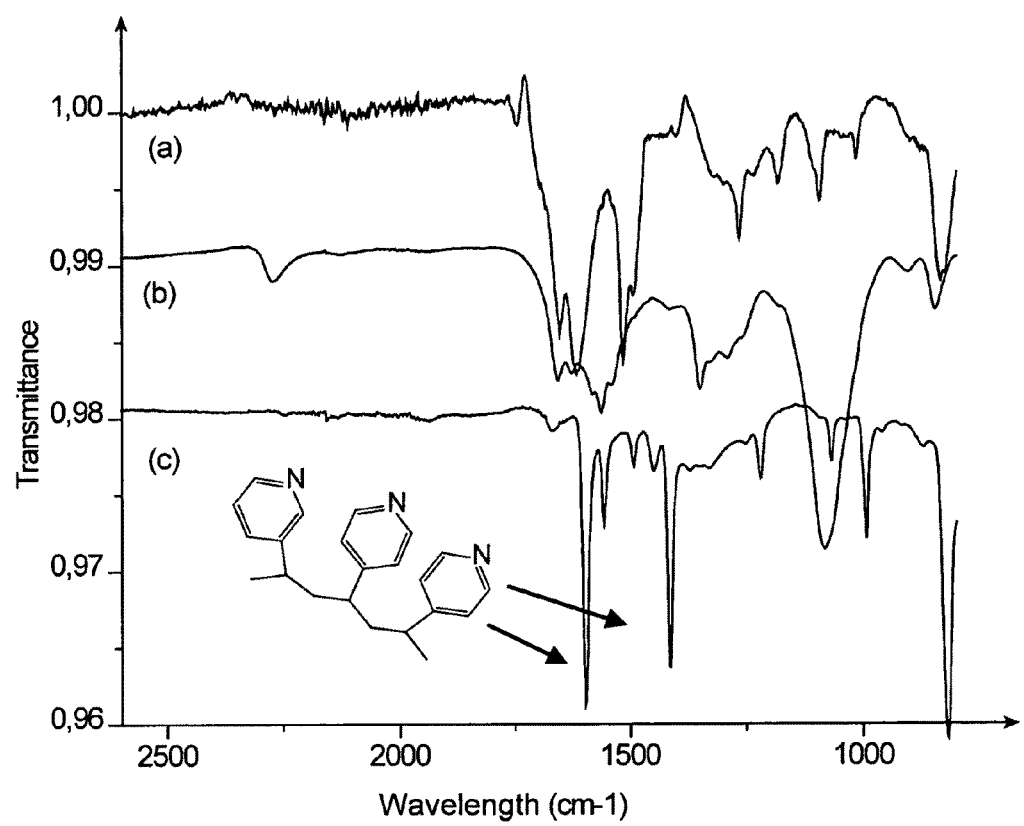
FIG. 13 shows the IR spectrum of a surface coated with a primer precursor of polyaminophenylene type (a), of a primer (b) and after reaction with poly-4-vinylpyridine (P4VP) (b).

FIG. 13 shows the IR spectra obtained for the primer surface (a) and the surface coated with P4VP (b). The characteristic peaks of the pyridine rings are present at about 1400 and 1600 cm$^{-1}$.
II-2-3 Dendrimers: PAMAM
Microscope slides comprising an adhesion primer, prepared according to the protocols outlined in I-2, were used.
PAMAM (Sigma-Aldrich) of formula:
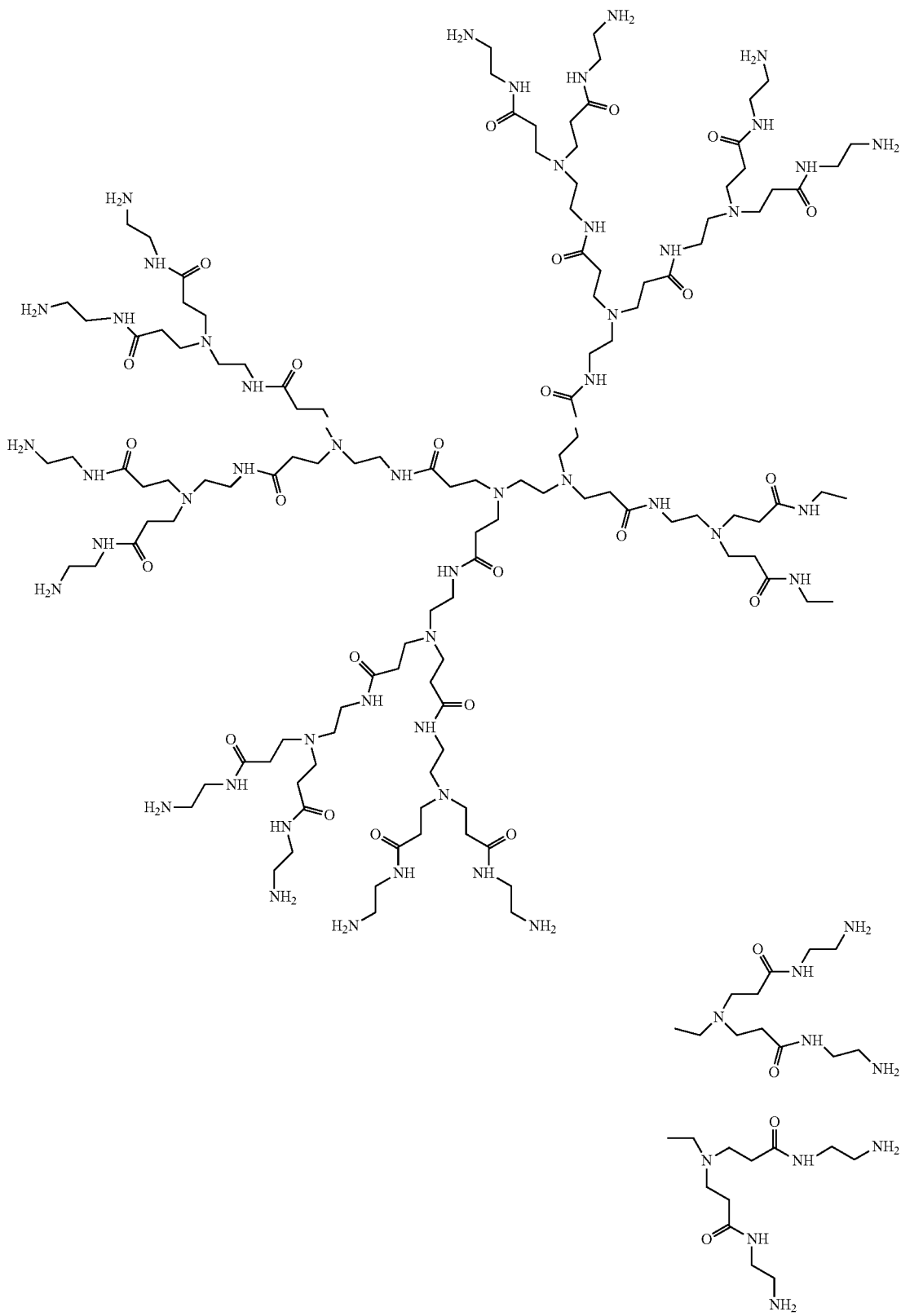

was dissolved to a proportion of 5% by mass in dimethylformamide (DMF) to achieve good dispersion. The microscope slides were placed on a spin coater and covered with the PAMAM solution. Spinning at 2000 rpm for one minute made it possible to form a thin film of PAMAM. 5 minutes after deposition, the slide was rinsed with HCl solution (0.5 M), with DMF and then with acetone.

Figure 14:
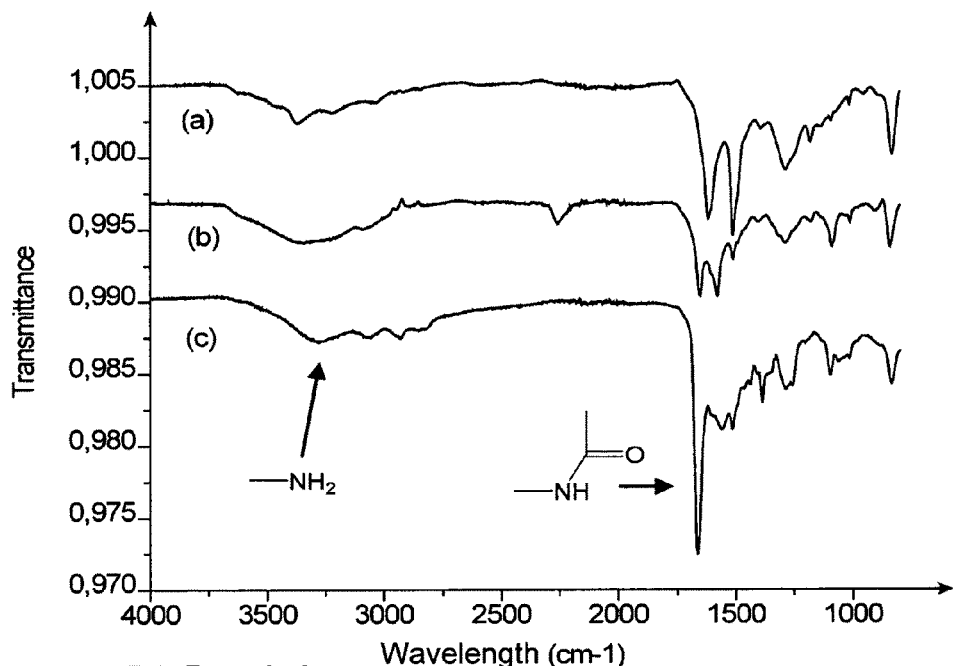
FIG. 14 shows the IR spectrum of a surface coated with a primer precursor of polyaminophenylene type (a), a primer (b) and after reaction with PAMAM (c).

On the IR spectra acquired after the reaction on the slides, the characteristic peaks of PAMAM may be seen: at about 3200 cm$^{-1}$ for the amines and 1670 cm$^{-1}$ for the amide functions (FIG. 14).

II-3 Immobilization of Biological Molecules

II-3-1 Study of the Stability Over Time

Microscope slides covered with a thin layer of gold about 100 nm thick were prepared by performing the treatment steps described in paragraphs I-1-1 (or I-1-2), I-2-2 and I-3. The slides thus treated will be referred to hereinbelow as "slides (or surfaces) coated with an activated self-adhesive layer".

The slides were immersed in pH 7 MilliQ water and then removed from the solution at different times and dried. These slides were then analysed by IR spectrometry. The intensity of the band at 2270 cm$^{-1}$ as a function of time was determined.

II-3-2 Immobilization of an Unprotected Linear Synthetic Peptide

The peptide GPGGVVGP (SEQ ID NO: 1 in the sequence listing given in the appendix) was synthesized using the 0.1 mmol Fmoc strategy. A preloaded commercial Fmoc-Gly-Wang resin (0.5 g, 0.8 mmol/g) is placed in the automatic peptide synthesizer reactor. The amino acids N$^\alpha$-Fmoc (Gly, Pro and Val) are used in a 10-fold excess with HBTU (O-benzotriazole-N,N,N',N'-tétraméthyl-uronium-hexafluoro-phosphate) in the presence of HOBT (N-hydroxybenzotriazole) and DIEA (N,N'-diisopropyldiethylamine) for 16 hours. 0.368 g of resin-bound peptide, which is deprotected at the N-spot end, is obtained.

The peptide is cleaved from the resin by means of a TFA/H$_2$O/TIS (trifluoroacetic acid/water/triisopropylesilane) solution (92:2.5:2.5) for 3 hours at room temperature. The resin is removed by filtration and is washed with TFA (2×1 mL) and dichloromethane (10 mL). The filtrate is evaporated under reduced pressure and then taken up in cold diethyl ether. After 12 hours at −20° C., a precipitate (100 mg) is isolated and collected after filtration. After purification by preparative HPLC chromatography, 39.5 mg of pure peptide are obtained.

2 mg of this peptide were dissolved in 1.5 mL of DMSO. 3×200 µL of this solution were deposited on three different samples: on a gold-covered microscope slide, on a slide coated with an activated self-adhesive layer, and on a surface coated with the "dead layer". The deposition was performed without any particular precautions, and at room temperature. After reaction for 10 minutes, the three supports are rinsed with DMSO and then subjected to washing under sonication: DMSO 2 minutes/ethanol 2 minutes/MilliQ water 2 minutes. The surface of the three supports were then dried under N$_2$. The three supports are analysed by IR spectrometry. The appearance of a band at 1670 cm$^{-1}$ (Amide I) on the support comprising the activated self-adhesive layer confirms the presence and covalent grafting of the peptide GPGGVVGP at the surface. The 1670 cm$^{-1}$ band specific for the peptide was not found on the gold support or on the "dead layer" support. These results confirm the covalent grafting of the peptide with the self-adhesive layer.

II-3-3 Immobilization of a Semi-Protected Synthetic Cyclic Peptide

Semi-protected CBO-P11 (SEQ ID NO: 2 in the sequence listing given in the appendix) of formula:

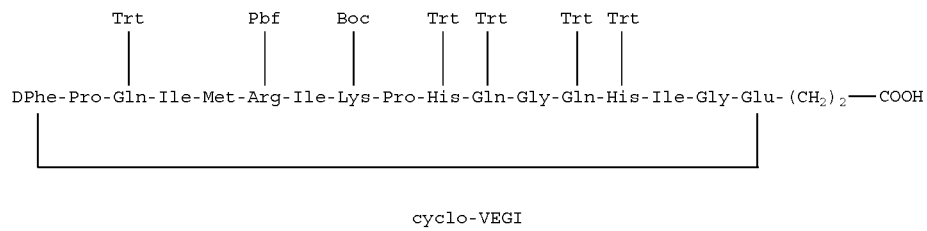

cyclo-VEGI was synthesized according to the method described in [Goncalves et al., 2005. *Pharmaceutical Research*, vol. 22, No. 8, pp. 1411-1421].

This semi-protected synthetic cyclic peptide was dissolved in DMSO (1 mg in 3 mL). 3×200 µL of this solution were deposited on three different samples: on a gold-covered microscope slide, on a slide coated with the activated self-adhesive layer, and on a surface coated with the "dead layer". The deposition was performed without any particular precautions, and at room temperature. After reaction for 10 minutes, the three supports are rinsed with DMSO and then subjected to washing under sonication: DMSO 2 minutes/ethanol 2 minutes/MilliQ water 2 minutes. The surface of the three supports is then dried under N$_2$. The three supports are analysed by IR spectrometry. The appearance of bands at 1666 cm$^{-1}$ (Amide I) and at 1534 cm$^{-1}$ (Amide II) on the support comprising the activated self-adhesive layer confirms the presence and covalent grafting of the semi-protected cyclic peptide at the surface.

The bands at 1666 cm$^{-1}$ (Amide I) and at 1534 cm$^{-1}$ (Amide II) specific for the peptide were found on the gold support and on the "dead layer" support with an intensity comparable to 10% of that measured on the support comprising the activated self-adhesive layer. This is due to the non-specific adsorption of the semi-protected cyclic peptide at the surface of these supports. The peptide adsorbed onto these supports may be removed by modifying the environmental conditions, for example the medium and/or its salinity. However, these results do indeed confirm the covalent grafting of the peptide with the self-adhesive layer.

II-3-4 Immobilization of an Unprotected Synthetic Cyclic Peptide

CBO-P11 (Calbiochem) of formula: cyclic(D-Phe-Pro-Gln-Ile-Met-Arg-Ile-Lys-Pro-His-Gln-Gly-Gln-His-Ile-Gly-Glu) (SEQ ID NO: 3 in the sequence listing given in the appendix) was dissolved in MilliQ water (1 mg in 3 mL). 3×200 µL of this solution were deposited on three different samples: on a gold-covered microscope slide, on a surface coated with the activated self-adhesive layer, and on a surface coated with the "dead layer". The deposition was performed without any particular precautions, and at room temperature. After reaction for 10 minutes, the three supports are rinsed with MilliQ water and then subjected to washing under sonication in MilliQ water for 2 minutes. The surface of the three supports is then dried under $N_2$. The three supports are analysed by IR spectrometry.

The appearance of bands at 1662 cm$^{-1}$ (Amide I) and at 1514 cm$^{-1}$ (Amide II) on the support comprising the activated self-adhesive layer confirms the presence and covalent grafting of the cyclic peptide (D-Phe-Pro-Gln-Ile-Met-Arg-Ile-Lys-Pro-His-Gln-Gly-Gln-His-Ile-Gly-Glu) (SEQ ID NO: 3 in the sequence listing given in the appendix) to the surface. The bands at 1662 cm$^{-1}$ (Amide I) and at 1514 cm$^{-1}$ (Amide II) specific for the peptide were found on the gold support and on the "dead layer" support with an intensity comparable to 10% of that measured on the support comprising the activated self-adhesive layer. This is due to the non-specific adsorption of CBO-P11 at the surface of the supports. The peptide adsorbed onto these supports may be removed by modifying the environmental conditions, for example the medium and/or its salinity. However, these results do indeed confirm the covalent grafting of the peptide with the self-adhesive layer.

II-3-5 Immobilization of monoamino-β-cyclodextrin

Monoamino-β-cyclodextrin was synthesized according to the procedure [Baugh et al., 2001. *J. Am. Soc. Chem.*, vol. 123 (50), 12488-12494]. 2 mg of monoamino-β-cyclodextrin were dissolved in 2 ml of MilliQ water. 3×200 μL of this solution were deposited on three different samples: on a gold-covered microscope slide, on a surface coated with the activated self-adhesive layer and on a surface coated with the "dead layer". The deposition was performed without any particular precautions, and at room temperature. After reaction for 10 minutes, the three supports are rinsed with MilliQ water and then subjected to washing under sonication: MilliQ water 2 minutes/ethanol 2 minutes/MilliQ water 2 minutes. The surface of the three supports is then dried under $N_2$. The three supports are analysed by IR spectrometry.

The appearance of bands at 1023, 1153, 2037 and 3321 cm$^{-1}$ on the support comprising the activated self-adhesive layer confirms the presence and covalent grafting of monoamino-β-cyclodextrin at the surface. The bands at 1023, 1153, 2037 and 3321 cm$^{-1}$ specific for β-cyclodextrin were not found on the gold support or on the "dead layer" support. These results confirm the covalent grafting of monoamino-β-cyclodextrin with the self-adhesive layer.

II-3-6 Immobilization of DNA

Low molecular weight salmon sperm DNA (Fluka) was dissolved in MilliQ water (1 mg in 3 mL). 3×200 μL of this solution were deposited on three different samples: on a gold-covered microscope slide, on a surface coated with the activated self-adhesive layer and on a surface coated with the "dead layer". The deposition was performed without any particular precautions, and at room temperature. After reaction for 10 minutes, the three supports are rinsed with MilliQ water and then subjected to washing under sonication: MilliQ water 2 minutes/ethanol 2 minutes/MilliQ water 2 minutes. The surface of the three supports was then dried under $N_2$. The three supports are analysed by IR spectrometry.

The appearance of bands at 1226 cm$^{-1}$ and at 1080 cm$^{-1}$ on the support comprising the activated self-adhesive layer confirms the presence and covalent grafting of DNA at the surface. The bands at 1226 cm$^{-1}$ and at 1080 cm$^{-1}$ specific for DNA were not found on the gold support or on the "dead layer" support. These results confirm the covalent grafting of DNA by the self-adhesive layer.

II-3-7 Immobilization of Glucose Oxidase on a Gold-Coated Microscope Slide

Glucose oxidase (Sigma-Aldrich) was dissolved in MilliQ water (1 mg in 3 mL). 3×200 μL of this solution were deposited on three different samples: on a gold-covered microscope slide, on a surface coated with the activated self-adhesive layer and on a surface coated with the "dead layer". The deposition was performed without any particular precautions, and at room temperature. After reaction for 10 minutes, the three supports are rinsed with MilliQ water and then subjected to washing under sonication: MilliQ water 2 minutes/ethanol 2 minutes/MilliQ water 2 minutes. The surface of the three supports is then dried under $N_2$. The three supports are analysed by IR spectrometry.

The appearance of bands at 1659 cm$^{-1}$ (Amide I), at 1546 cm$^{-1}$ (Amide II) and at 1225 cm$^{-1}$ (Amide III) on the support comprising the activated self-adhesive layer confirms the presence and covalent grafting of glucose oxidase at the surface. The bands at 1659 cm$^{-1}$ (Amide I), at 1546 cm$^{-1}$ (Amide II) and at 1255 cm$^{-1}$ (Amide III) specific for glucose oxidase were not found on the gold support or on the "dead layer" support. These results confirm the covalent grafting of glucose oxidase with the self-adhesive layer.

A support bearing glucose oxidase obtained as described above was immersed in a reactor containing a solution of PBS buffer at pH 7 in a volume equal to 13 mL. The support was connected to a potentiostat. The system comprises a counter-electrode (composed of a graphite plate) and a reference electrode of the SCE (saturated calomel electrode) type. The electrode was subjected to a potential sweep of cyclic voltammetry type at a rate of 20 mV·s$^{-1}$ between the equilibrium potential (typically observed between 0.1 and 0.3 V) and +0.750 mV on the outward sweep, and then a return sweep down to −0.2 V and finally a return to the equilibrium potential where the voltage was switched off. The limit potential values of the cyclic voltammetry were determined by the controlled addition of $H_2O_2$ (and in the absence of glucose oxidase) to the medium in order to determine the zone of electroactivity of $H_2O_2$. A first current measurement was taken without glucose, and makes it possible to obtain the reference for the system. After adding glucose, the current is measured at −0.200 mV and at +0.500 mV. The current variation was monitored over time. Two different glucose concentrations were used: 7.69×10$^{-4}$ M and 7.69×10$^{-3}$ M.

It is very clearly seen that the appearance of $H_2O_2$ as a function of time does indeed follow a law of the increasing hyperbolic type that is compatible with the Michaelis-Menton relationship. When the solution containing glucose was replaced with a solution of PBS buffer, a decreasing hyperbole appeared over time until a voltammetry spectrum identical to the reference spectrum was obtained.

| | [Glc] = 7.69 × 10$^{-4}$ M | | | | |
|---|---|---|---|---|---|
| | 1 min | 7 min | 20 min | 40 min | 60 min |
| ΔI (a.u.) | 0.39 | 1.05 | 6.82 | 18.68 | 31.38 |

For a glucose concentration of 7.69×10$^{-4}$ M, the initial reaction rate is 0.4916 a.u./min.

| [Glc] = 7.69 × 10⁻³ M | | | | | |
|---|---|---|---|---|---|
| | 11 min | 31 min | 41 min | 51 min | 61 min | 81 min |
| ΔI (a.u.) | 10.18 | 20.98 | 29.48 | 35.68 | 38.88 | 42.38 |

For a glucose concentration of $7.69 \times 10^{-3}$ M, the initial reaction rate is 0.9255 a.u./min.

By plotting the graph as double inverse 1/initial rate=f(1/[glucose]), an observed Michaelis constant $K_m$ of the order of 113 mM was determined. This result is in accordance with the $K_m$ values for glucose oxidase found in the literature ($K_m$=33-115 mM).

II-3-8 Immobilization of Glucose Oxidase on Polyvinylidene Fluoride (PVDF)

Strips of PVDF β were prepared by performing the treatment steps described in paragraphs I-1-1 (or I-1-2), I-2-2 and I-3. Glucose oxidase (Sigma-Aldrich) was dissolved in MilliQ water (1 mg in 3 mL). 2×200 μL of this solution were deposited on two different samples: on a strip of blank PVDF β and on a surface coated with the activated self-adhesive layer. The deposition was performed without any particular precautions, and at room temperature. After reaction for 10 minutes, the two supports are rinsed with MilliQ water and then subjected to washing under sonication: MilliQ water 2 minutes/ethanol 2 minutes/MilliQ water 2 minutes. The surface of the two supports is then dried under $N_2$. The two supports are analysed by IR spectrometry.

The appearance of a band at 1659 cm$^{-1}$ (Amide I) on the support comprising the activated self-adhesive layer confirms the presence and covalent grafting of glucose oxidase to the surface. The band at 1659 cm$^{-1}$ (Amide I) specific for glucose oxidase was not found on the strip of blank PVDF β. These results confirm the covalent grafting of glucose oxidase with the self-adhesive layer.

III—Use of the Process According to the Invention for Modifying the Surface Energy of a Surface III-1 Grafting Strategy Used The synthesis is performed in three steps.

In the first step, 1,4-aminophenyldiazonium (obtained in situ by oxidation of 1,4-diaminophenylene with sodium nitrite) has been grafted. In the second step, the grafted amine functions were diazotized via the action of sodium nitrite. In the final step, the surface, now comprising diazonium salt, has been placed in contact (40° C.<T<70° C., UV, reducing agent) with a hydrophobic molecule (Zonyl®) and the modified surface, bearing chemically bonded hydrophobic molecules, has been obtained.

III-2 Reagents

The reagents used in this example are as follows:

1,4-diaminophenylene: F.W.=108.14; m=0.324 g; n=3 mmol; 1 eq.

sodium nitrite: F.W.=68.995; m=0.207 g; n=3 mmol; 1 eq.

HCl: F.W.=36.46; C=4 M; v=20 mL $H_2O$: v=15 mL iron powder: F.W.=55.85; m=1.0 g; n=18 mmol; 1 eq.

Zonyl®: F.W.=443; d=1.17; v=2 mL; n=7.7 mmol; 1 eq.

III-3 Protocol

Step 1: 1,4-Diaminophenylene (0.324 g, $3 \times 10^{-3}$ mol) was dissolved in a solution of hydrochloric acid (20 mL of 4 M) in a 50 mL beaker with magnetic stirring at room temperature. 15 mL of aqueous sodium nitrite solution (0.207 g, $3 \times 10^{-3}$ mol) were added cautiously to this pale yellow solution to give a Bordeaux-red solution. Two glass slides and one gold slide used as reference for checking by IR the grafting efficacy were then immersed in the bath. Iron powder (1.0 g, $18 \times 10^{-3}$ mol) was then added. The glass and gold slides were removed after 180 minutes and then rinsed successively with MilliQ water, ethanol and acetone, and dipped in a bath of DMF at 60° C. for 15 minutes before beginning the IR analyses.

Step 2: The pregrafted slides were immersed in 0.1 M sodium nitrite solution (25 mL) diluted in 25 mL of 0.5 M HCl solution for 1 minute. These slides were rinsed with water and then dried under a stream of argon before the IR analyses.

Step 3: The slides were finally dipped in Zonyl® at 35° C. for 1 hour, rinsed and analysed by IR.

III-4 Results

Figure 15:
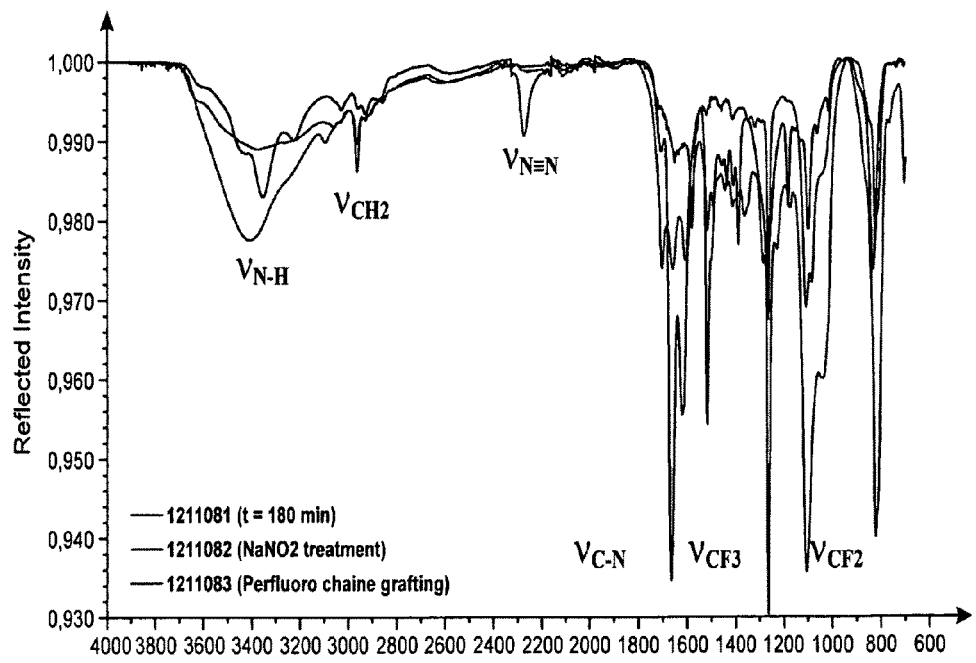
FIG. 15 shows the analysis by IR spectrometry of gold covered microscope slide onto which has been grafted, by radical chemical grafting, for 180 minutes, a film of a primer precursor of supported phenylamine type (1211081), of a primer of supported phenyldiazonium type (1211082) and after reaction of this primer with a hydrophobic molecule, namely Zonyl® (1211083).

The analysis by IR spectrometry of the gold slides after step 1 confirmed the presence of the expected film (FIG. 15, 1211081). The specific bands at 3342 cm$^{-1}$ (NH stretching), 1665 cm$^{-1}$ and 1616 cm$^{-1}$ (C—N stretching) are visible. An estimation of the coating thicknesses (percentage of grafting) was obtained by measuring the percentage of absorption of the most intense band of the spectrum, in this case the C—N at 1616 cm$^{-1}$.

The conversions of the amine functions into diazoniums (step 2) and then of the diazoniums into fluoro ethers (step 3) was also confirmed by IR (bands at 2268 cm$^{-1}$ for N≡N; 1103 and 1263 cm$^{-1}$ for $CF_3$ and $CF_2$) (FIG. 15, 1211082 and 1211083).

Files:

1211081 (t=180 minutes, gold) 6.1% grafting 1211082 (NaNO$_2$ treatment)

1211083 (perfluoro chain grafting).

Figure 16:
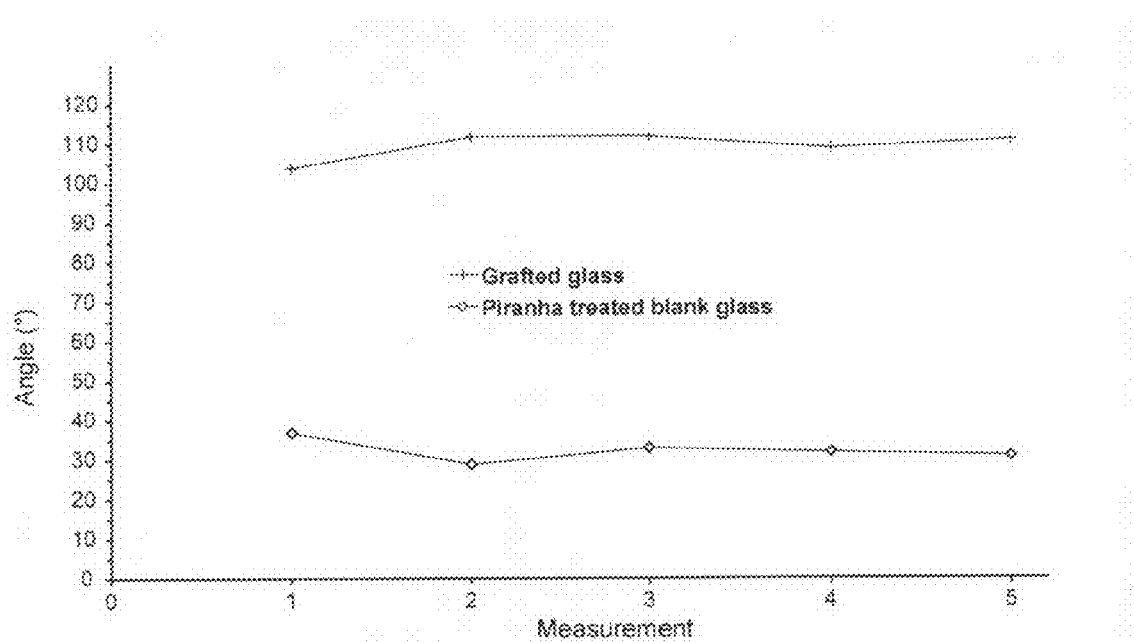
FIG. 16 shows the measured contact angle (five independent measurements) for a drop of water on glass slides onto which has been grafted a perfluoro chain derived from Zonyl® according to the process described in point III-3, a blank glass slide serving as control.
Figure 17A:
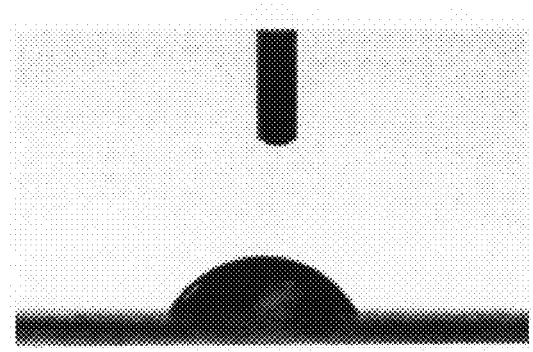
FIG. 17 is a photograph of a drop of water on a blank glass slide (FIG. 17A) and that of a drop of water on a glass slide onto which has been grafted a perfluoro chain derived from Zonyl® according to the process described in point III-3 (FIG. 17B).
Figure 17B:
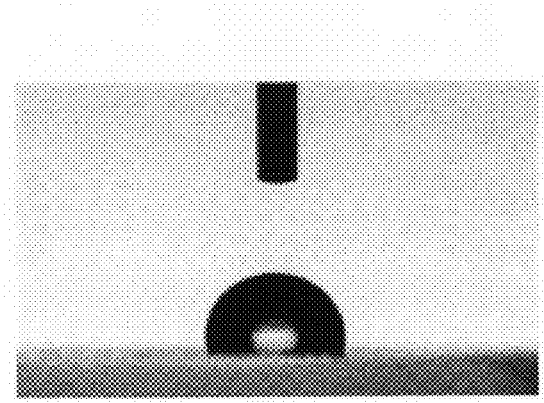

FIG. 16 shows the contact angle values obtained for a drop of water placed on a blank glass slide or on a glass slide onto which has been grafted a perfluoro chain derived from Zonyl® according to the process described in point III-3 (five independent measurements). FIG. 17 is a photograph of this drop on a blank glass slide (FIG. 17A) or on a glass slide thus grafted (FIG. 17B).

The invention claimed is:

1. A method for assembling at least one zone of a first surface with at least one zone of a second surface or with a molecule of interest, comprising the following successive steps:
   a) optionally subjecting a zone of the said first surface bearing at least one adhesion primer precursor to conditions suitable for obtaining, from an adhesion primer precursor, at least one adhesion primer,
   b) subjecting the said zone of said first surface bearing at least one adhesion primer optionally obtained in step (a) to non-electrochemical conditions to obtain, on said zone of said first surface, at least one radical species; and
   c) placing the said zone of the said first surface bearing at least one radical species, obtained in step (b), in contact with the said zone of the said second surface or with the said molecule of interest
   wherein said first surface bearing at least one adhesion primer is of formula (I) below:

(first surface)-(B)$_n$—R—N$_2^+$,A$^-$      (I)

in which:
   (B)$_n$ represents a bonding agent,
   n is equal to 1, and B represents a bonding agent in the form of a polymer or copolymer, derived from several units of identical or different chemical species,
   A represents a monovalent anion, and
   R represents an aryl group.

2. The method according to claim 1, wherein the molecule of interest is chosen from the group constituted by organic molecules comprising weak organic bases, organic macromolecules, biological molecules and hydrophobic molecules.

3. The method according to claim 1, wherein said adhesion primer is chosen from the group constituted by supported phenyldiazonium tetrafluoroborate, supported 4-nitrophenyldiazonium tetrafluoroborate, supported 4-bromophenyldiazonium tetrafluoroborate, supported 4-aminophenyldiazonium chloride, supported 2-methyl-4-chlorophenyldiazonium chloride, supported 4-benzoylbenzenediazonium tetrafluoroborate, supported 4-cyanophenyldiazonium tetrafluoroborate, supported 4-carboxyphenyldiazonium tetrafluoroborate, supported acetamidophenyldiazonium tetrafluoroborate, supported 4-phenylacetic acid diazonium tetrafluoroborate, supported 2-methyl-4-[(2-methylphenyl)diazenyl]benzenediazonium sulfate, supported 9,10-dioxo-9,10-dihydro-1-anthracenediazonium chloride, supported 4-nitronaphthalenediazonium tetrafluoroborate and supported naphthalenediazonium tetrafluoroborate.

4. The method according to claim 1, wherein said non-electrochemical conditions are chosen from the group constituted by thermal, kinetic, chemical, photochemical and radiochemical conditions, and combinations thereof.

5. The method according to claim 1, wherein said placing in contact is performed in solution.

6. The method according to claim 1, wherein said zone of said first surface bearing at least one adhesion primer precursor is a zone of said first surface to which is bonded covalently, an organic film bearing at least one adhesion primer precursor.

7. The method according to claim 1, wherein said adhesion primer precursor is chosen from the group constituted by supported phenylamine, supported 4-nitrophenylamine, supported 4-bromophenylamine, supported 4-amino phenylamine, supported 2-methyl-4-chlorophenylamine, supported 4-benzylbenzeneamine, supported 4-cyanophenylamine, supported 4-carboxyphenylamine, supported 4-acetamidophenylamine, supported 4-aminobenzoic acid, supported 2-methyl-4-[(2-methylphenyl)diazenyl]amine, supported 9,10-dioxo-9,10-dihydro-1-anthraceneamine, supported 4-nitronaphthaleneamine and supported naphthaleneamine.

8. A process for modifying the surface energy of at least one surface of a solid, which comprises assembling the said surface with a hydrophobic molecule according to an assembling process as defined in claim 1.

9. A process for modifying the surface energy of at least one surface of a solid, which comprises assembling the said surface with a hydrophobic molecule according to an assembling process as defined in claim 1, and wherein said process comprises an additional step, following the said assembling, of subjecting the surface assembled with the said molecule to a heat treatment.

10. A method for assembling at least one zone of a first surface with at least one zone of a second surface or with a molecule of interest, comprising the following steps:
   a) optionally subjecting a zone of the said first surface bearing at least one adhesion primer precursor to conditions suitable for obtaining, from an adhesion primer precursor, at least one adhesion primer,
   b) subjecting the said zone of said first surface bearing at least one adhesion primer optionally obtained in step (a) to non-electrochemical conditions to obtain, on said zone of said first surface, at least one radical species; and
   c) placing the said zone of the said first surface bearing at least one radical species, obtained in step (b), in contact with the said zone of the said second surface or with the said molecule of interest
   wherein said steps (b) and (c) are performed simultaneously
   wherein said first surface bearing at least one adhesion primer is of formula (I) below:

(first surface)-(B)$_n$—R—N$_2^+$,A$^-$      (I)

in which:
   (B)$_n$ represents a bonding agent,
   n is equal to 1, and B represents a bonding agent in the form of a polymer or copolymer, derived from several units of identical or different chemical species,
   A represents a monovalent anion, and
   R represents an aryl group.

* * * * *